(12) United States Patent
Sakaguchi et al.

(10) Patent No.: US 11,180,515 B2
(45) Date of Patent: *Nov. 23, 2021

(54) NON-AQUEOUS ELECTROLYTIC SOLUTION FOR POWER STORAGE ELEMENT

(71) Applicant: STELLA CHEMIFA CORPORATION, Osaka (JP)

(72) Inventors: Toshitaka Sakaguchi, Sakai (JP); Sojiro Kon, Sakai (JP); Yoshifumi Katsura, Sakai (JP); Masashi Yamamoto, Sakai (JP); Tetsuo Nishida, Sakai (JP)

(73) Assignee: Stella Chemifa Corporation, Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 17/010,611

(22) Filed: Sep. 2, 2020

(65) Prior Publication Data

US 2020/0399296 A1 Dec. 24, 2020

Related U.S. Application Data

(62) Division of application No. 15/751,841, filed as application No. PCT/JP2016/073462 on Aug. 9, 2016, now Pat. No. 10,793,585.

(30) Foreign Application Priority Data

Aug. 10, 2015 (JP) .............................. JP2015-158572

(51) Int. Cl.
*C07F 9/11* (2006.01)
*H01M 10/054* (2010.01)
*H01M 10/0567* (2010.01)
*C07F 9/09* (2006.01)
*H01M 10/052* (2010.01)
*H01G 11/64* (2013.01)
*H01M 10/0568* (2010.01)
*C07F 9/12* (2006.01)
*C07H 15/252* (2006.01)
*H01M 4/587* (2010.01)
*H01M 10/0525* (2010.01)
*H01M 10/0569* (2010.01)

(52) U.S. Cl.
CPC ...... *C07F 9/11* (2013.01); *C07F 9/09* (2013.01); *C07F 9/091* (2013.01); *C07F 9/092* (2013.01); *C07F 9/12* (2013.01); *C07H 15/252* (2013.01); *H01G 11/64* (2013.01); *H01M 4/587* (2013.01); *H01M 10/052* (2013.01); *H01M 10/054* (2013.01); *H01M 10/0525* (2013.01); *H01M 10/0567* (2013.01); *H01M 10/0568* (2013.01); *H01M 10/0569* (2013.01); *Y02E 60/13* (2013.01)

(58) Field of Classification Search
CPC ......................................................... C07F 9/11
See application file for complete search history.

(56) References Cited

U.S. PATENT DOCUMENTS 4,185,111 A 1/1980 Ducep et al.
10,793,585 B2 * 10/2020 Sakaguchi .......... H01M 10/052

FOREIGN PATENT DOCUMENTS

| AT | 500478 A | 3/1980 |
| AU | 3791178 A | 7/1978 |
| BE | 868888 A | 1/1979 |
| CN | 103066324 A | 4/2013 |
| CN | 103762334 A | 4/2014 |
| DE | 2830488 A1 | 1/1979 |
| FR | 2397425 A1 | 2/1979 |
| GB | 2001987 A | 2/1979 |

(Continued)

OTHER PUBLICATIONS

Extended European Search Report received in European Patent Application No. 16835184.9 dated Mar. 25, 2019.
Garrigou-Lagrange, C., et al., Conformational Analysis of Dialkyl Phosphates, Canadian Journal of Spectroscopy 21 (3):75-82, 1976, Abstract.
Hummel, M., et al., Non-Halide Ionic Liquids for Solvation, Extraction, and Processing of Cellulosic Materials, In Cellulose Solvents: For Analysis, Shaping and Chemical Modification, Liebert., T., et al., Chapter 13, ACS Symposium Series, American Chemical Society, Washington, D.C., 2010, pp. 229-259.
Keiper, J.S., et al., Self-Assembly of Phosphate Fluorosurfactants in Carbon Dioxide, Langmuir 20:1065-1072, 2004.

(Continued)

*Primary Examiner* — Golam M Shameem
(74) *Attorney, Agent, or Firm* — Knobbe, Martens, Olson & Bear, LLP

(57) ABSTRACT

A non-aqueous electrolytic solution includes a phosphoric acid diester salt, which can suppress deterioration of charge-discharge characteristics of a power storage element, and can suppress the rise in internal resistance after storage at high temperature. The phosphoric acid diester salt is represented by the following chemical formula (1):

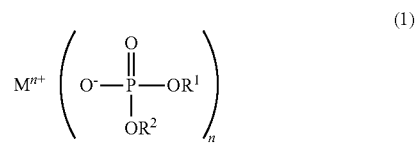

in which $M^{n+}$ represents a hydrogen ion, an alkali metal ion, an alkali earth metal ion, an aluminum ion, a transition metal ion, or an onium ion, $R^1$ and $R^2$ are different from each other and represent a hydrocarbon group having 1 to 10 carbon atoms, or a hydrocarbon group having 1 to 10 carbon atoms and having at least one of a halogen atom, a heteroatom, and an unsaturated bond, and n represents a valence.

5 Claims, 2 Drawing Sheets

(56) References Cited

FOREIGN PATENT DOCUMENTS

| | | | |
|---|---|---|---|
| IT | 1096695 | A | 8/1985 |
| JP | 54-19959 | A | 2/1979 |
| JP | 2012-1459 | A | 1/2012 |
| JP | 2014-12649 | A | 1/2014 |
| NL | 7807215 | A | 1/1979 |
| WO | WO 2009/020912 | A2 | 2/2009 |
| WO | WO 2010/109889 | A1 | 3/2010 |
| WO | WO 2015/122512 | A1 | 8/2015 |
| WO | WO 2015/122519 | A1 | 8/2015 |
| ZA | 7803939 | A | 7/1978 |

OTHER PUBLICATIONS

Mahajna, M., et al., Thermal Fragmentation of Trihaloethyl and Hexafluoro-2-propyl (α-hydroxyiminobenzyl)phosphonates. Solvent Effects and the Trapping of Metaphosphate, Journal of Organic Chemistry 58(27):7822-7826, 1993.

Mahmood, T., et al., Polyfluoroalkyl dibasic acid phosphates, bis(polyfluoroalkyl) monobasic acid phosphates, and Their Precursors, Inorganic Chemistry 25(21):3830-3837, 1986.

Office Action issued in CN application No. 201680044466.9., dated Sep. 2, 2019.

Office Action issued in CN application No. 201680044466.9., dated May 26, 2020.

RN 61599-31-3 Registry, copyright 2019.

RN 693214-08-03, Registry ((STN)).

RN 771448-74-9, Registry ((STN)).

* cited by examiner

NON-AQUEOUS ELECTROLYTIC SOLUTION FOR POWER STORAGE ELEMENT

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention relates to a phosphoric acid diester salt, a production method therefor, a non-aqueous electrolytic solution for a power storage element, and a power storage element, and more particularly to a phosphoric acid diester salt which can improve charge-discharge characteristics of a power storage element when the phosphoric acid diester salt is applied to the power storage element, and can suppress the rise in internal resistance after storage at high temperature, a production method therefor, a non-aqueous electrolytic solution for a power storage element, and a power storage element.

Description of the Related Art

Examples of a power storage element using a non-aqueous electrolytic solution include secondary batteries such as a lithium ion secondary battery, capacitors such as an electric double layer capacitor and the like. Of these power storage elements, the lithium ion secondary battery has already been put to practical use widely as power sources of portable telephones and personal computers, and demand for the lithium ion secondary battery been increasing. However, since numerous raw materials including expensive metals such as lithium are used in the lithium ion secondary battery, there is concern about the raw materials that might be supplied in response to the increase in demand.

Meanwhile, a sodium ion secondary battery has attracted much attention as a secondary battery that solves concern about the supply of the raw materials, and a study has been made. The sodium ion secondary battery has higher Clarke number than that of lithium and uses sodium, an abundant resource, as a main constituent material, so that it is expected that the sodium ion secondary battery contributes to solving of concern about the supply and cost reduction.

In these power storage elements, regarding use environment temperature thereof, there is a need to have higher durability than conventional one under both high temperature environment and low temperature environment. Because of enlargement of cells under high temperature environment, the cells are steadily exposed to comparatively high temperature due to not only use environment but also self-heating, so that an improvement in durability at high temperature is very important. When the power storage element is stored under high temperature environment, the internal resistance of the cells rises as an electrode, an electrolytic solution, and an electrolyte deteriorate, leading to significant energy loss which originates in internal resistance under low temperature environment.

In an alkali metal ion secondary battery among power storage elements, it is generally interpreted that a stable film (solid electrolyte interface) is formed, which has alkali metal ion conductivity but has no electron conductivity, at an interface between the electrode active material and the electrolytic solution. However, when the alkali metal ion secondary battery is stored under high temperature environment, its stable film sometimes causes cracking, dissolution, or decomposition, thus resulting in a problem such as deterioration of charge-discharge characteristics of the alkali metal ion secondary battery, or increase in impedance.

There has been proposed, as a sodium ion secondary battery among alkali metal ion batteries, a sodium ion secondary battery in which a non-aqueous solvent of a saturated cyclic carbonate or a mixture of a saturated cyclic carbonate and a chain carbonate is used as an electrolytic solution, and hard carbon is used as a negative electrode active material (Patent Document 1 mentioned below). It is mentioned that this sodium ion secondary battery is operable at normal temperature and can suppress deterioration of battery performance that is caused by the negative electrode active material. However, there is a problem that the sodium ion secondary battery exhibits insufficient storage characteristics under high temperature environment and charge-discharge characteristics after storage deteriorate, and the internal resistance rises.

PRIOR ART DOCUMENTS

Patent Documents

Patent Document 1: WO 2010/109889 A

SUMMARY OF THE INVENTION

Problems to be Solved by the Invention

In light of the above problems, the present invention has been made and an object thereof is to provide a phosphoric acid diester salt which can suppress deterioration of charge-discharge characteristics of a power storage element, and can suppress the rise in internal resistance after storage at high temperature, a production method therefor, a non-aqueous electrolytic solution for a power storage element, and a power storage element.

Solutions to the Problems

To solve the above problems, the phosphoric acid diester salt of the present invention is characterized by a phosphoric acid diester salt represented by the following chemical formula (1):

[Chemical Formula 1]

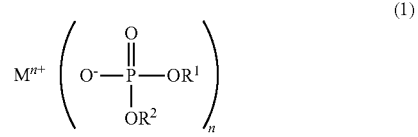

(1)

wherein $M^{n+}$ represents a hydrogen ion, an alkali metal ion, an alkali earth metal ion, an aluminum ion, a transition metal ion, or an onium ion; $R^1$ and $R^2$ are different from each other and represent a hydrocarbon group having 1 to 10 carbon atoms, or a hydrocarbon group having 1 to 10 carbon atoms and having at least one of a halogen atom, a heteroatom, and an unsaturated bond; and n represents a valence.

In the above configuration, either one of $R^1$ and $R^2$ is preferably an alkyl group having 1 to 10 carbon atoms and having a halogen atom, and other one is preferably an alkyl group having 1 to 10 carbon atoms and having no halogen atom.

In the above configuration, either one of $R^1$ and $R^2$ is preferably a 2,2,2-trifluoroethyl group, and other one is preferably an ethyl group.

In the above configuration, M is preferably at least one selected from the group consisting of lithium, sodium, magnesium, and calcium.

In the above configuration, M is preferably triethylmethylammonium, tetraethylammonium, 1-ethyl-3-methylimidazolium, or 1-ethyl-2methylpyrrolidinium.

To solve the above problems, the method for producing a phosphoric acid diester salt of the present invention is characterized by including the steps of: producing a phosphoric acid diester by hydrolyzing a phosphoric acid triester represented by the chemical formula (2) mentioned below; and producing a phosphoric acid diester salt represented by the chemical formula (1) mentioned below by reacting the phosphoric acid diester with $M^{n+}(OH)n$ (in which $M^{n+}$ represents a hydrogen ion, an alkali metal ion, an alkali earth metal ion, an aluminum ion, a transition metal ion, or an onium ion, and n represents a valence); wherein a $—OR^1$ group and a $—OR^2$ group in the phosphoric acid triester are leaving groups, and leaving ability of the $—OR^1$ group is larger than leaving ability of the $—OR^2$ group:

[Chemical Formula 2]

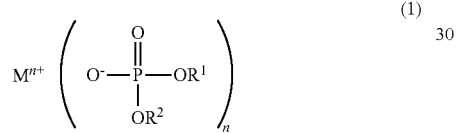

(1)

wherein $M^{n+}$ represents a hydrogen ion, an alkali metal ion, an alkali earth metal ion, an aluminum ion, a transition metal ion, or an onium ion; $R^1$ and $R^2$ are different from each other and represent a hydrocarbon group having 1 to 10 carbon atoms, or a hydrocarbon group having 1 to 10 carbon atoms and having at least one of a halogen atom, a heteroatom, and an unsaturated bond; and n represents a valence: and

[Chemical Formula 3]

(2)

wherein $R^1$ and $R^2$ are different from each other and represent a hydrocarbon group having 1 to 10 carbon atoms, or a hydrocarbon group having 1 to 10 carbon atoms and having at least one of a halogen atom, a heteroatom, and an unsaturated bond.

In the above configuration, either one of $R^1$ and $R^2$ is preferably an alkyl group having 1 to 10 carbon atoms and having a halogen atom, and other one is preferably an alkyl group having 1 to 10 carbon atoms and having no halogen atom.

Either one of $R^1$ and $R^2$ is preferably a 2,2,2-trifluoroethyl group, and other one is preferably an ethyl group.

To solve the above problems, the non-aqueous electrolytic solution for a power storage element of the present invention is characterized by including, as an additive, a phosphoric acid diester salt represented by the following chemical formula (1):

[Chemical Formula 4]

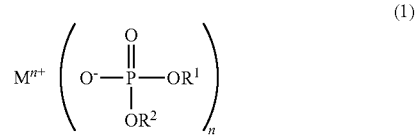

(1)

wherein $M^{n+}$ represents a hydrogen ion, an alkali metal ion, an alkali earth metal ion, an aluminum ion, a transition metal ion, or an onium ion; $R^1$ and $R^2$ are different from each other and represent a hydrocarbon group having 1 to 10 carbon atoms, or a hydrocarbon group having 1 to 10 carbon atoms and having at least one of a halogen atom, a heteroatom, and an unsaturated bond; and n represents a valence.

To solve the above problems, the non-aqueous electrolytic solution for a power storage element of the present invention is characterized by including, as an electrolyte, a phosphoric acid diester salt represented by the following chemical formula (1):

[Chemical Formula 5]

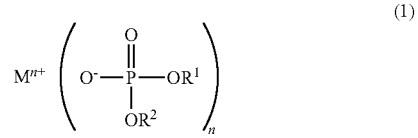

(1)

wherein $M^{n+}$ represents a hydrogen ion, an alkali metal ion, an alkali earth metal ion, an aluminum ion, a transition metal ion, or an onium ion; $R^1$ and $R^2$ are different from each other and represent a hydrocarbon group having 1 to 10 carbon atoms, or a hydrocarbon group having 1 to 10 carbon atoms and having at least one of a halogen atom, a heteroatom, and an unsaturated bond; and n represents a valence.

In the above configuration, either one of $R^1$ and $R^2$ is preferably an alkyl group having 1 to 10 carbon atoms and having a halogen atom, and other one is preferably an alkyl group having 1 to 10 carbon atoms and having no halogen atom.

In the above configuration, either one of $R^1$ and $R^2$ is preferably a 2,2,2-trifluoroethyl group, and other one is preferably an ethyl group.

In the above configuration, M is preferably at least one selected from the group consisting of lithium, sodium, magnesium, and calcium.

In the above configuration, M is preferably triethylmethylammonium, tetraethylammonium, 1-ethyl-3-methylimidazolium, or 1-ethyl-2methylpyrrolidinium.

To solve the above problems, the power storage element of the present invention is characterized by using a non-aqueous electrolytic solution including, as an additive, a phosphoric acid diester salt represented by the following chemical formula (1):

[Chemical Formula 6]

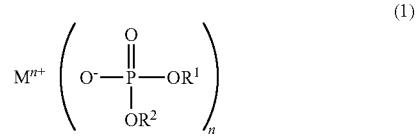

(1)

wherein $M^{n+}$ represents a hydrogen ion, an alkali metal ion, an alkali earth metal ion, an aluminum ion, a transition metal ion, or an onium ion; $R^1$ and $R^2$ are different from each other and represent a hydrocarbon group having 1 to 10 carbon atoms, or a hydrocarbon group having 1 to 10 carbon atoms and having at least one of a halogen atom, a heteroatom, and an unsaturated bond; and n represents a valence.

To solve the above problems, the power storage element of the present invention is characterized by using a non-aqueous electrolytic solution including, as an electrolyte, a phosphoric acid diester salt represented by the following chemical formula (1):

[Chemical Formula 7]

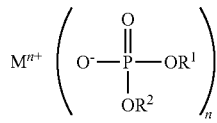
(1)

wherein $M^{n+}$ represents a hydrogen ion, an alkali metal ion, an alkali earth metal ion, an aluminum ion, a transition metal ion, or an onium ion; $R^1$ and $R^2$ are different from each other and represent a hydrocarbon group having 1 to 10 carbon atoms, or a hydrocarbon group having 1 to 10 carbon atoms and having at least one of a halogen atom, a heteroatom, and an unsaturated bond; and n represents a valence.

Effects of the Invention

According to the present invention, when using a phosphoric acid diester salt represented by the chemical formula (1) as an electrolyte or an additive in a non-aqueous electrolytic solution, it is possible to improve charge-discharge characteristics of a power storage element using the non-aqueous electrolytic solution, and to suppress the rise in internal resistance even after storage at high temperature.

Figure 1:
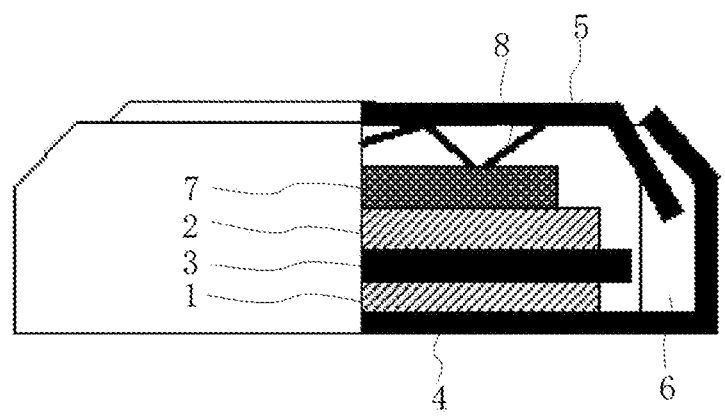
FIG. 1 is a schematic sectional view which schematically illustrates a sodium ion secondary battery according to an embodiment of the present invention in which an additive of the present embodiment is added to an electrolytic solution for a non-aqueous electrolytic solution.

DETAILED DESCRIPTION OF THE PREFERRED EMBODIMENT (Phosphoric Acid Diester Salt)

First, a phosphoric acid diester salt according to the present embodiment will be described below. The phosphoric acid diester salt is represented by the following chemical formula (1).

[Chemical Formula 8]

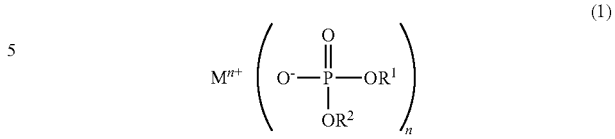
(1)

In the chemical formula (1), $M^{n+}$ represents a hydrogen ion, an alkali metal ion, an alkali earth metal ion, an aluminum ion, a transition metal ion, or an onium ion.

Examples of the alkali metal ion include, but are not limited to, lithium ion, sodium ion, potassium ion, rubidium ion, cesium ion and the like.

Examples of the alkali earth metal ion include magnesium ion, calcium ion, strontium ion, barium ion and the like.

Examples of the transition metal ion include, but are not limited to, manganese ion, cobalt ion, nickel ion, chromium ion, copper ion, molybdenum ion, tungsten ion, vanadium ion and the like.

Examples of the onium ion include ammonium ion ($NH^{4+}$), primary ammonium ion, secondary ammonium ion, tertiary ammonium ion, quaternary ammonium ion, quaternary phosphonium ion, sulfonium ion and the like.

Examples of the primary ammonium ion include, but are not limited to, methylammonium ion, ethylammonium ion, propylammonium ion, isopropylammonium ion and the like.

Examples of the secondary ammonium ion include, but are not limited to, dimethylammonium ion, diethylammonium ion, dipropylammonium ion, dibutylammonium ion, ethylmethylammonium ion, methylpropylammonium ion, methylbutylammonium ion, propylbutylammonium ion, diisopropylammonium ion and the like.

Examples of tertiary ammonium which forms the tertiary ammonium ion include, but are not limited to, trimethylammonium ion, triethylammonium ion, tripropylammoniummammonium ion, tributylammonium ion, ethyldimethylammonium ion, diethylmethylammonium ion, triisopropylammonium ion, dimethylisopropylammonium ion, diethylisopropylammonium ion, dimethylpropylammonium ion, butyldimethylammonium ion, 1-methylpyrrolidinium ion, 1-ethylpyrrolidinium ion, 1-propylpyrrolidinium ion, 1-butylpropylpyrrolidinium ion, 1-methylimidazolium ion, 1-ethylimidazolium ion, 1-propylimidazolium ion, 1-butylimidazolium ion, pyrazolium ion, 1-methylpyrazolium ion, 1-ethylpyrazolium ion, 1-propylpyrazolium ion, 1-butylpyrazolium ion, pyridinium ion and the like.

Examples of quaternary ammonium which forms the quaternary ammonium ion include, but are not limited to, aliphatic quaternary ammoniums, imidazoliums, pyridiniums, pyrazoliums, pyridaziniums and the like.

Examples of the aliphatic quaternary ammoniums include, but are not limited to, tetraethylammonium, tetrapropylammonium, tetraisopropylammonium, trimethylethylammonium, dimethyldiethylammonium, methyltriethylammonium, trimethylpropylammonium, trimethylisopropylammonium, tetrabutylammonium, trimethylbutylammonium, trimethylpentylammonium, trimethylhexylammonium, 1-ethyl-1-methyl-pyrrolidinium, 1-butyl-1-methylpyrrolidinium, 1-ethyl-1-methyl-piperidinium, 1-butyl-1-methylpiperidinium and the like.

Examples of the imidazoliums include, but are not limited to, 1,3dimethyl-imidazolium, 1-ethyl-3-methylimidazolium, 1-n-propyl-3-methylimidazolium, 1-n-butyl-3-methylimidazolium, 1-n-hexyl-3-methylimidazolium and the like.

Examples of the pyridiniums include, but are not limited to, 1-methylpyridinium, 1-ethylpyridinium, 1-n-propylpyridinium and the like.

Examples of the pyrazoliums include, but are not limited to, 1,2-dimethylpyrazolium, 1-methyl-2-ethylpyrazolium, 1-propyl-2-methylpyrazolium, 1-methyl-2-butylpyrazolium, 1-methylpyrazolium, 3-methylpyrazolium, 4-methylpyrazolium, 4-iodopyrazolium, 4-bromopyrazolium, 4-iodo-3-methylpyrazolium, 4-bromo-3-methylpyrazolium, 3-trifluoromethylpyrazolium and the like.

Examples of the pyridaziniums include, but are not limited to, 1-methylpyridazinium, 1-ethylpyridazinium, 1-propylpyridazinium, 1-butylpyridazinium, 3-methylpyridazinium, 4-methylpyridazinium, 3-methoxypyridazinium, 3,6-dichloropyridazinium, 3,6-dichloro-4-methylpyridazinium, 3-chloro-6-methylpyridazinium, 3-chloro-6-methoxypyridazinium and the like.

Examples of quaternary phosphonium which forms the quaternary phosphonium ion include, but are not limited to, benzyltriphenylphosphonium, tetraethylphosphonium, tetraphenylphosphonium and the like.

Examples of the sulfonium ion include, but are not limited to, trimethylsulfonium, triphenylsulfonium, triethylsulfonium and the like.

Among those listed as $M^{n+}$, $M^{n+}$ is preferably lithium ion, sodium ion, magnesium ion, calcium ion, tetraalkylammonium ion, alkylimidazolium ion, or alkylpyrrolidinium ion, from the viewpoint of availability.

In the chemical formula (1), $R^1$ and $R^2$ are functional groups which are different from each other. $R^1$ and $R^2$ represent a hydrocarbon group, or a hydrocarbon group having at least one of a halogen atom, a heteroatom, and an unsaturated bond (hereinafter referred to as "hydrocarbon group having a halogen atom, etc."). The hydrocarbon group has 1 to 10 carbon atoms, and preferably 1 to 4 carbon atoms. The hydrocarbon group having a halogen atom has 1 to 10 carbon atoms, and preferably 1 to 4 carbon atoms. The number of unsaturated bonds is preferably in a range of 1 to 10, more preferably 1 to 5, and particularly preferably 1 to 3.

Specific examples of the hydrocarbon group or the hydrocarbon group having a halogen atom include chain alkyl groups such as a methyl group, an ethyl group, a propyl group, a butyl group, an isopropyl group, a pentyl group, a hexyl group, a heptyl group, and an octyl group; cyclic alkyl groups such as a cyclopentyl group and a cyclohexyl group; chain halogen-containing alkyl groups such as a 2-iodoethyl group, a 2-bromoethyl group, a 2-chloroethyl group, a 2-fluoroethyl group, a 1,2-diiodoethyl group, a 1,2-dibromoethyl group, a 1,2-dichloroethyl group, a 1,2-difluoroethyl group, a 2,2-diiodoethyl group, a 2,2-dibromoethyl group, a 2,2-dichloroethyl group, a 2,2-difluoroethyl group, a 2,2,2-tribromoethyl group, a 2,2,2-trichloroethyl group, a 2,2,2-trifluoroethyl group, and a hexafluoro-2-propyl group; cyclic halogen-containing alkyl groups such as a 2-iodocyclohexyl group, a 2-bromocyclohexyl group, a 2-chlorocyclohexyl group, and a 2-fluorocyclohexyl group; chain alkenyl groups such as a 2-propenyl group, an isopropenyl group, a 2-butenyl group, and a 3-butenyl group; cyclic alkenyl groups such as a 2-cyclopentenyl group, a 2-cyclohexenyl group, and a 3-cyclohexenyl group; chain alkynyl groups such as a 2-propynyl group, a 1-butynyl group, a 2-butynyl group, a 3-butynyl group, a 1-pentynyl group, a 2-pentynyl group, a 3-pentynyl group, and a 4-pentynyl group; phenyl groups such as a phenyl group, a 3-methoxyphenyl group, a 4-methoxyphenyl group, a 3,5-dimethoxyphenyl group, and a 4-phenoxyphenyl group; halogen-containing phenyl group such as a 2-iodophenyl group, a 2-bromophenyl group, a 2-chlorophenyl group, a 2-fluorophenyl group, a 3-iodophenyl group, a 3-bromophenyl group, a 3-chlorophenyl group, a 3-fluorophenyl group, a 4-iodophenyl group, a 4-bromophenyl group, a 4-chlorophenyl group, a 4-fluorophenyl group, a 3,5-diiodophenyl group, a 3,5-dibromophenyl group, a 3,5-dichlorophenyl group, and a 3,5-difluorophenyl group; and naphthyl groups such as a 1-naphthyl group, a 2-naphthyl group, and a 3-amino-2-naphthyl group.

The halogen atom means an atom of fluorine, chlorine, bromine, or iodine. The hydrocarbon group having a halogen atom means that hydrogens in the hydrocarbon group may be partially or entirely substituted with any one of these halogen atoms. The heteroatom means an atom of oxygen, nitrogen, or sulfur. The hydrocarbon group having a heteroatom means that hydrogens and carbons in the hydrocarbon group may be partially or entirely substituted with any one of these heteroatoms.

Specific examples of the hydrocarbon group having a heteroatom include a 2-methoxyethyl group, a 2-(2-methoxyethoxy)ethyl group, a 2-(2-(2-methoxyethoxy)ethoxy)ethyl group, a 2-(2-(2-(2-methoxyethoxy)ethoxy)ethoxy)ethyl group and the like.

From the viewpoint of the solubility in an organic solvent having high polarity (for example, a non-aqueous solvent such as propylene carbonate or ethylene carbonate, details will be mentioned in the description of an additive for a non-aqueous electrolytic solution of a power storage element according to the present embodiment), the phosphoric acid diester anion is preferably a phosphoric acid diester anion in which an anion structure is polarized and the dipole moment as the degree of polarization is as high as possible. From such point of view, either one of $R^1$ and $R^2$ is preferably an alkyl group having 1 to 10 carbon atoms and having a halogen atom, and other one is preferably an alkyl group having 1 to 10 carbon atoms and having no halogen atom. Examples of the alkyl group having 1 to 10 carbon atoms and having a halogen atom include a fluorine-containing alkyl group. The fluorine-containing alkyl group is not particularly limited and may be of straight-chain, branched, or cyclic. Specific examples thereof include a trifluoromethyl group, a 2-fluoroethyl group, a 2,2-difluoroethyl group, a 2,2,2-trifluoroethyl group, a 2,2,3,3-tetrafluoropropyl group, a 2,2,3,3,3-pentafluoropropyl group, a hexafluoroisopropyl group, a 2,2,3,3,4,4,5,5-octafluoropentyl group, a 2,2,3,3,4,4,5,5,6,6,7,7-dodecafluoroheptyl group, a 3,3,4,4,5,5,6,6,7,7,8,8,9,9,10,10,10-heptadecafluorodecyl group and the like. From the viewpoint of availability of the raw material, a 2,2,2-trifluoroethyl group is preferable among these fluorine-containing alkyl groups. When the fluorine-containing alkyl group is a 2,2,2-trifluoroethyl group, the alkyl group having 1 to 10 carbon atoms and having no halogen atom is preferably an ethyl group, from the viewpoint of availability of the raw material. The alkyl group having a halogen atom more preferably has 1 to 4 carbon atoms. The alkyl group having no halogen atom more preferably has 1 to 4 carbon atoms.

Specific examples of the phosphoric acid diester anion in which $R^1$ and $R^2$ are composed only of alkyl groups which are different from each other include ethylmethylphosphoric acid anion, ethylpropylphosphoric acid anion, methylpropylphosphoric acid anion and the like.

Specific examples of the phosphoric acid diester anion in which either one of $R^1$ and $R^2$ is an alkyl group having a halogen atom, and the other one is an alkyl group having no halogen atom include (2,2,2-trichloroethyl)ethylphosphoric acid anion, (2,2,2-trichloroethyl)methylphosphoric acid anion, hexachloroisopropylethylphosphoric acid anion, hexachloroisopropylmethylphosphoric acid anion, (2,2,2-trifluoroethyl)ethylphosphoric acid anion, (2,2,2-trifluoroethyl) methylphosphoric acid anion, hexafluoroisopropylethylphosphoric acid anion, hexafluoroisopropylmethylphosphoric acid anion and the like.

Specific examples of the phosphoric acid diester in which either one of $R^1$ and $R^2$ is an alkyl group having a heteroatom, and the other one is an alkyl group include methyl(2-methoxyethyl)phosphoric acid anion, methyl(2-(2-methoxyethoxy)ethyl)phosphoric acid anion, methyl(2-(2-(2-methoxyethoxy)ethoxy)ethyl)phosphoric acid anion, methyl (2-(2-(2-(2-methoxyethoxy)ethoxy)ethoxy)ethyl) phosphoric acid anion and the like.

In the chemical formula (1), n represents a valence. For example, n=1 when M is a monovalent cation, n=2 when M is a divalent cation, and n=3 when M is a trivalent cation.

Specific examples of the phosphoric acid diester salt represented by the chemical formula (1) include sodium ethyl methyl phosphate, sodium ethyl propyl phosphate, sodium ethyl(2,2,2-trichloroethyl)phosphate, sodium methyl(2,2,2-trichloroethyl)phosphate, sodium ethyl hexachloroisopropyl phosphate, sodium ethyl(2,2,2-trifluoroethyl)phosphate, sodium methyl(2,2,2-trifluoroethyl)phosphate, sodium ethyl(2,2,2-trifluoroethyl)phosphate, sodium ethyl hexafluoroisopropyl phosphate, sodium methyl(2-methoxyethyl)phosphate, sodium methyl(2-(2-methoxyethoxy)ethyl)phosphate, sodium methyl(2-(2-(2-methoxyethoxy)ethoxy)ethyl)phosphate, sodium methyl(2-(2-(2-(2-methoxyethoxy)ethoxy)ethoxy)ethyl)phosphate, 1-ethyl-3-methylimidazoliumethylmethylphosphoric acid, 1-ethyl-3-methylimidazoliumethylpropylphosphoric acid, 1-ethyl-3-methylimidazoliumethyl(2,2,2-trichloroethyl)phosphoric acid, 1-ethyl-3-methylimidazoliummethyl(2,2,2-trichloroethyl)phosphoric acid, 1-ethyl-3-methylimidazoliumethylhexachloroisopropylphosphoric acid, 1-ethyl-3-methylimidazoliumethyl(2,2,2-trifluoroethyl)phosphoric acid, 1-ethyl-3-methylimidazoliummethyl(2,2,2-trifluoroethyl)phosphoric acid, 1-ethyl-3-methylimidazoliumethyl(2,2,2-trifluoroethyl)phosphoric acid, 1-ethyl-3-methylimidazoliumethylhexafluoroisopropylphosphoric acid, 1-ethyl-3-methylimidazoliummethyl(2-methoxyethyl)phosphoric acid, 1-ethyl-3-methylimidazoliummethyl(2-(2-methoxyethoxy) ethyl)phosphoric acid, 1-ethyl-3-methylimidazoliummethyl(2-(2-(2-methoxyethoxy)ethoxy)ethyl)phosphoric acid, 1-ethyl-3-methylimidazoliummethyl(2-(2-(2-(2-methoxyethoxy)ethoxy)ethoxy)ethyl)phosphoric acid, triethylmethylammoniumethylmethylphosphoric acid, triethylmethylammoniumethylpropylphosphoric acid, triethylmethylammoniumethyl(2,2,2-trichloroethyl)phosphoric acid, triethylmethylammoniummethyl(2,2,2-trichloroethyl)phosphoric acid, triethylmethylammoniumethylhexachloroisopropylphosphoric acid, triethylmethylammonium ethyl(2,2,2-trifluoroethyl)phosphoric acid, triethylmethylammoniummethyl(2,2,2-trifluoroethyl)phosphoric acid, triethylmethylammonium ethyl(2,2,2-trifluoroethyl)phosphoric acid, triethylmethylammoniumethylhexafluoroisopropylphosphoric acid, triethylmethylammoniummethyl(2-methoxyethyl) phosphoric acid, triethylmethylammoniummethyl(2-(2-methoxyethoxy)ethyl)phosphoric acid, triethylmethylammoniummethyl(2-(2-(2-methoxyethoxy)ethoxy)ethyl) phosphoric acid, triethylmethylammoniummethyl(2-(2-(2-(2-methoxyethoxy)ethoxy)ethoxy)ethyl)phosphoric acid and the like.

(Method for Producing Phosphoric Acid Diester Salt)

Next, a description will be made of a method for producing a phosphoric acid diester salt according to the present embodiment.

The method for producing a phosphoric acid diester salt of the present embodiment includes at least a step A of producing a phosphoric acid diester by hydrolyzing a phosphoric acid triester represented by the chemical formula (2) mentioned below; and a step B of producing a phosphoric acid diester salt represented by the chemical formula (1) mentioned below by reacting the phosphoric acid diester with $M^{n+}(OH)_n$ (in which $M^{n+}$ represents, a hydrogen ion, an alkali metal ion, an alkali earth metal ion, an aluminum ion, a transition metal ion, or an onium ion, and n represents a valence, hereinafter referred to as "hydroxide").

[Chemical Formula 9]

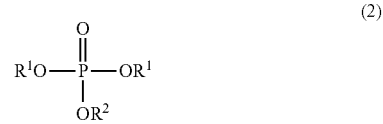

(2)

In the chemical formula (2), $R^1$ and $R^2$ are as already described hereinabove, and are the same as $R^1$ and $R^2$ in the chemical formula (1). Therefore, detailed description thereof is omitted.

The phosphoric acid triester can be hydrolyzed, for example, in the presence of water. Whereby, a reaction as shown in the following chemical scheme (1) arises to produce a phosphoric acid diester.

[Chemical Formula 10]

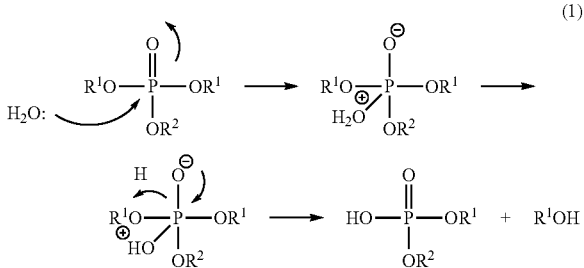

(1)

Furthermore, by reacting a phosphoric acid diester with the hydroxide, a reaction represented by the following chemical scheme (2) arises to produce a phosphoric acid diester salt.

[Chemical Formula 11]

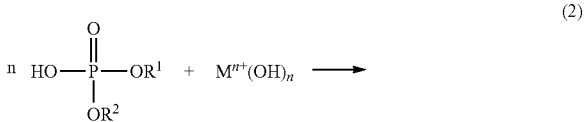

(2)

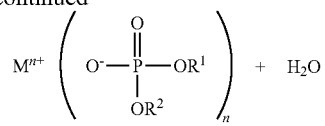

The steps A and B can be performed at a time by reacting the hydroxide with the phosphoric acid triester in the presence of water. Also in this case, first, as shown in the chemical scheme (1), hydrolysis between the phosphoric acid triester and water arises to produce a phosphoric acid diester. Thereafter, as shown in the chemical scheme (2), it is presumed that a phosphoric acid diester reacts with a hydroxide to produce a phosphoric acid diester salt. Namely, it is considered that, by subjecting a phosphor atom of the phosphoric acid triester to nucleophilic attack by water, a phosphoric acid diester is produced first, and then a salt is obtained by a neutralization reaction with a hydroxide.

When the hydroxide is reacted with the phosphoric acid triester in the presence of water to produce a phosphoric acid diester salt at a time, there is a need that leaving ability of a $-OR^1$ group of the phosphoric acid triester as a raw material is larger than leaving ability of a $-OR^2$ group. The reason is that the $-OR^1$ group of the phosphoric acid triester must be eliminated first due to hydrolysis. Whereby, it is made possible to obtain a phosphoric acid diester salt of the present embodiment in which $R^1$ and $R^2$ are different from each other and are arranged asymmetrically.

The leaving ability of the $-OR^1$ group and the $-OR^2$ group as a leaving group can be roughly presumed by the pKa value of each protonated form thereof. Namely, the pKa value of $H-OR^1$ is preferably smaller than that of $H-OR^2$. The pKa value can be estimated by the Bordwell pKa Table. Alternatively, it is possible to presume that those including an electron-withdrawing group in the leaving group have high leaving ability.

When the hydroxide is reacted with the phosphoric acid triester in the presence of water to produce a phosphoric acid diester salt at a time, regarding a reaction ratio of the hydroxide to the phosphoric acid triester, the amount of the hydroxide is preferably at least 0.5 equivalent or more, more preferably 0.5 equivalent to 1 equivalent, still more preferably 0.8 equivalent to 1 equivalent, and particularly preferably 0.9 equivalent to 0.95 equivalent, based on 1 equivalent of the phosphoric acid triester. When the use amount of the phosphoric acid triester is set at 0.5 equivalent or more, it is possible to prevent the reactivity between the phosphoric acid triester and the hydroxide from deteriorating and to suppress the unreacted hydroxide from remaining, thus making it possible to suppress purity of the phosphoric acid diester salt from being lowered. The upper limit of the use amount of the phosphoric acid triester is not particularly limited. However, the use of the phosphoric acid triester in an excessive amount requires production time and energy more than necessary when this phosphoric acid triester is distilled off, thus resulting in an industrial disadvantage. It is therefore preferred to appropriately set the upper limit of the use amount of the phosphoric acid triester in accordance with the reactive species or reaction scales.

When the reaction between the phosphoric acid triester and the hydroxide is started in the presence of water, the reaction starting temperature is not particularly limited as long as the reaction proceeds and the reaction starting temperature may be appropriately set in accordance with the reactive species. Usually, the reaction starting temperature is in a range of 0 to 200° C. From the viewpoint of the reactivity, the reaction starting temperature is in a range of 20 to 150° C., and more preferably 40 to 120° C. When the reaction starting temperature is set at 0° C. or higher, the reaction rate can be prevented from being remarkably attenuated. Meanwhile, when the reaction starting temperature is set at 200° C. or lower, energy loss due to use of excess energy can be suppressed. The method for adjusting the reaction starting temperature is not particularly limited. When the system is cooled to control so as to set the reaction starting temperature in the above-mentioned temperature range, control can be made by ice cooling of a reaction vessel including the phosphoric acid triester and hydroxide charged therein. When the system is heated to control so as to set the reaction starting temperature in the above-mentioned temperature range, control can be made by an oil bath set at an arbitrary temperature.

When the phosphoric acid triester is reacted with the hydroxide in the presence of water, the reaction time is not particularly limited, and the reaction time may be appropriately set in accordance with the reactive species. Usually, the reaction times are preferably in a range of 30 minutes to 10 hours. From the viewpoint of industrial production, the reaction time is preferably in a range of 30 minutes to 5 hours, and more preferably 30 minutes to 3 hours.

In the reaction between the phosphoric acid triester and the hydroxide, water, an organic solvent, or the phosphoric acid triester can be used as a reaction solvent. When using an organic solvent or a phosphoric acid triester as the reaction solvent, the reaction between the phosphoric acid triester and the hydroxide is performed in a state where water is allowed to be present in the organic solvent or phosphoric acid triester.

The organic solvent is not particularly limited as long the organic solvent does not cause a trouble that the reaction solvent reacts with other reactants or reaction products. Specific examples thereof include alcohols, nitriles, esters, ketones, ethers, halogenated hydrocarbons and the like. These organic solvents can be used alone or in combination of two or more thereof.

Examples of the alcohols include, but are not limited to, methanol, ethanol, propanol, butanol, isopropyl alcohol, pentanol, hexanol, heptanol, octanol, 2-iodoethanol, 2-bromoethanol, 2-chloroethanol, 2-fluoroethanol, 1,2-diiodoethanol, 1,2-dibromoethanol, 1,2-dichloroethanol, 1,2-difluoroethanol, 2,2-diiodoethanol, 2,2-dibromoethanol, 2,2-dichloroethanol, 2,2-difluoroethanol, 2,2,2-tribromoethanol, 2,2,2-trichloroethanol, 2,2,2-trifluoroethanol, hexafluoroisopropyl alcohol, ethylene glycol monomethyl ether, diethylene glycol monomethyl ether, triethylene glycol monomethyl ether, tetraethylene glycol monomethyl ether and the like. These alcohols can be used alone or in combination of two or more thereof.

Examples of the nitriles include, but are not limited to, acetonitrile, propionitrile and the like. These nitriles can be used alone or in combination of two or more thereof.

Examples of the esters include, but are not limited to, dimethyl carbonate, diethyl carbonate, ethylmethyl carbonate, ethylene carbonate, propylene carbonate, ethyl acetate, methyl acetate, butyl acetate and the like. These esters can be used alone or in combination of two or more thereof.

Examples of the ketones include, but are not limited to, acetone, methyl ethyl ketone, methyl isobutyl ketone, cyclohexanone and the like. These ketones can be used alone or in combination of two or more thereof.

Examples of the ethers include, but are not limited to, diethyl ether, tetrahydrofuran, dimethoxyethane and the like. These ethers can be used alone or in combination of two or more thereof.

Examples of the halogenated hydrocarbon include, but are not limited to, dichloromethane, chloroform and the like. These halogenated hydrocarbons can be used alone or in combination of two or more thereof.

Other examples of the organic solvent include nitromethane, nitroethane, dimethylformamide and the like.

The use amount of the organic solvent is preferably at least 1 time, more preferably 1 to 200 times, still more preferably 1 to 100 times, and particularly preferably 1 to 50 times, the mass of the phosphoric acid triester. When the use amount of the organic solvent is adjusted at at least 1 time the mass of the phosphoric acid triester, it is possible to prevent the reactivity between the phosphoric acid triester and the hydroxide from deteriorating and to suppress the unreacted hydroxide from remaining, thus making it possible to suppress yield and purity of the phosphoric acid diester salt from being lowered. The upper limit of the use amount of the organic solvent is not particularly limited. However, the use of the organic solvent in an excessive amount requires energy more than necessary when this solvent is distilled off, thus resulting in an industrial disadvantage. It is therefore preferred to appropriately set the upper limit of the use amount of the organic solvent in accordance with the reactive species.

The use amount of water as the reaction solvent is preferably 0.5 equivalent or more, and more preferably 1 equivalent or more, based on 1 equivalent of the phosphoric acid triester. When the use amount of water is set at 0.5 equivalent or more, it is possible to prevent the reactivity between the phosphoric acid triester and the hydroxide from deteriorating and to suppress the unreacted hydroxide from remaining, thus making it possible to suppress purity of the phosphoric acid diester salt from being lowered. The upper limit of the use amount of water is not particularly limited. However, the use of water in an excessive amount requires production time and energy more than necessary when this water is distilled off, thus resulting in an industrial disadvantage. It is therefore preferred to appropriately set the upper limit of the use amount of water in accordance with the reactive species or reaction scales.

When water is contained in the organic solvent as the reaction solvent or the phosphoric acid triester, the content of water is preferably in a range of 0.5 equivalent to 100 equivalents, more preferably 1 equivalent to 50 equivalents, and still more preferably 1 equivalent to 10 equivalents, based on 1 equivalent of the phosphoric acid triester. When the content of water is set at 0.5 equivalent or more, it is possible to prevent the reactivity between the phosphoric acid triester and the hydroxide from deteriorating and to suppress the unreacted phosphoric acid triester from remaining, thus making it possible to suppress purity of the phosphoric acid diester salt from being lowered. Meanwhile, when the content of water is set at 100 equivalents or less, it is possible to suppress energy required to remove excess water.

When using an organic solvent as the reaction solvent, the order of the addition of a phosphoric acid triester, a hydroxide, and water is not particularly limited. When using water as the reaction solvent, the order of the addition of a phosphoric acid triester and a hydroxide is not particularly limited. When using a phosphoric acid triester as the reaction solvent, the order of the addition of water and a hydroxide is not particularly limited.

Regarding the phosphoric acid diester salt obtained by the method of the present embodiment, it is also possible to produce a phosphoric acid diester salt having desired different kinds of cations by performing cation exchange utilizing the solubility, or cation exchange using an ion exchange resin.

It is also possible to produce a phosphoric acid diester by reacting the phosphoric acid diester salt obtained by the method of the present embodiment with Arrhenius acid such as sulfuric acid or hydrochloric acid. It is also possible to obtain a phosphoric acid diester by performing proton exchange using an ion exchange resin. It is also possible to produce a phosphoric acid diester salt by reacting the phosphoric acid diester obtained by this method with a halide or a hydroxide.

In the present embodiment, immediately after the step of producing a phosphoric acid diester salt, the step of purifying the phosphoric acid diester salt may be performed. By subjecting the phosphoric acid diester salt to cation exchange, purification can be performed immediately after the step of producing a phosphoric acid diester salt having different kinds of cations. Immediately after reacting the phosphoric acid diester with the halide to produce a phosphoric acid diester salt, purification can be performed. The purification method is not particularly limited, and it is possible to employ a method by an operation such as distillation or drying, or a method using an adsorbent such as active carbon or an ion exchange resin. Purity of the phosphoric acid diester salt can be enhanced by performing such purification.

(Method for Producing Phosphoric Acid Triester)

It is possible to produce a phosphoric acid triester represented by the above chemical formula (2) serving as a starting material of the phosphoric acid diester salt of the present embodiment by various methods.

For example, the phosphoric acid triester can be produced by reacting a monohalophosphoric acid diester represented by the following chemical formula (3) with a hydroxy compound in the other organic solvent or in the absence of a solvent:

[Chemical Formula 12]

(3)

wherein $R^1$ is the same as defined in the chemical formula (1), and X represents I, Br, Cl or the like.

Examples of the hydroxy compound include, but are not limited to, alcohols, phenols, naphthols, saccharides and the like. These hydroxy compounds listed may be appropriately selected in accordance with in accordance with the usage of the phosphodiester salt, which is an intended product. From the viewpoint of availability, among these hydroxy compounds, alcohols can be suitably used.

Examples of the alcohols include, but are not limited to, chain alkyl alcohols such as methanol, ethanol, propanol, butanol, isopropyl alcohol, pentanol, hexanol, heptanol, and octanol; cyclic alkyl alcohols such as cyclopentanol and cyclohexanol; chain halogen-containing alcohols such as 2-iodoethanol, 2-bromoethanol, 2-chloroethanol, 2-fluoroethanol, 1,2-diiodoethanol, 1,2-dibromoethanol, 1,2-dichloroethanol, 1,2-difluoroethanol, 2,2-diiodoethanol, 2,2-dibromoethanol, 2,2-dichloroethanol, 2,2-difluoroethanol, 2,2,2-tribromoethanol, 2,2,2-trichloroethanol, 2,2,2-trifluoroethanol, and hexafluoroisopropyl alcohol; cyclic halogen-containing alkyl alcohols such as 2-iodocyclohexanol, 2-bromocyclohexanol, 2-chlorocyclohexanol, and 2-fluorocyclohexanol; chain alkenyl alcohols such as 2-propenol, isopropenol, 2-butenyl alcohol, and 3-butenyl alcohol; cyclic alkenyl alcohols such as 2-cyclopenten-1-ol, 2-cyclohexen-1-ol, and 3-cyclohexen-1-ol; chain alkynyl alcohols such as 2-propynyl alcohol, 1-butynyl alcohol, 2-butynyl alcohol, 3-butynyl alcohol, 1-pentynyl alcohol, 2-pentynyl alcohol, 3-pentynyl alcohol, and 4-pentynyl alcohol; and alcohols having a hetero element, such as ethylene glycol monomethyl ether, diethylene glycol monomethyl ether, triethylene glycol monomethyl ether, and tetraethylene glycol monomethyl ether. It is preferred to appropriately select from among these alcohols such that the leaving ability of the —OR$^1$ group becomes larger than the leaving ability of the —OR$^2$ group. These alcohols can be used alone or in combination of two or more thereof.

The other organic solvent is not particularly limited, and it is preferred to use the hydroxy compound or an aprotic organic solvent. When using a hydroxy compound as the other organic solvent, it is preferred to use a hydroxy compound which is the same as the hydroxy compound as a raw material. When using, as the other organic solvent, a hydroxy compound which is different from the hydroxy compound as a raw material, the side reaction may cause production of those other than desired phosphoric acid triester, leading to lowered yield.

Examples of the aprotic organic solvent include, but are not limited to, nitriles, esters, ketones, ethers, halogenated hydrocarbons and the like. These aprotic organic solvents can be used alone or in combination of two or more thereof.

The use amount of the other organic solvent is preferably at least 2 times, more preferably 2 to 100 times, and still more preferably 2 to 50 times, the mass of the monohalophosphoric acid diester. When the use amount of the other organic solvent is adjusted at at least 2 times the mass of the monohalophosphoric acid diester, the reaction between the monohalophosphoric acid ester and the hydroxy compound can be efficiently performed. The upper limit of the use amount of the other organic solvent is not particularly limited. However, the use of the organic solvent in an excessive amount requires energy more than necessary when this organic solvent is distilled off, thus resulting in an industrial disadvantage. It is therefore preferred to appropriately set the upper limit of the use amount of the organic solvent in accordance with the reactive species.

The use amount of the hydroxy compound as the raw material is preferably in a range of 1 equivalent to 5 equivalents, more preferably 1 equivalent to 3 equivalents, and still more preferably 1.05 equivalents to 1.1 equivalents, based on 1 equivalent of the monohalophosphoric acid diester. When the use amount of the hydroxy compound is set at 1 equivalent or more, it is possible to prevent the monohalophosphoric acid diester as the raw material from remaining. The upper limit of the use amount of the hydroxy compound is not particularly limited. However, the use of the hydroxy compound in an amount of more than 5 equivalent requires energy more than necessary when the excess hydroxy compound is distilled off. It is therefore preferred to appropriately set the upper limit of the use amount of the hydroxy compound in accordance with the reactive species.

When the reaction between the monohalophosphoric acid diester and the hydroxide is started, the reaction starting temperature is not particularly limited as long as the reaction proceeds. Usually, the reaction starting temperature is in a range of −20° C. or higher and 200° C. or lower, preferably 15° C. or higher and 100° C. or lower, and more preferably 0° C. or higher and lower than 50° C. When the reaction starting temperature is set at 200° C. or lower, it is possible to suppress yield of the hydroxy compound from lowering due to vaporization and to prevent purity of the phosphoric acid triester as the product from lowering. Meanwhile, when the reaction starting temperature is set at −20° C. or higher, it is possible to prevent the monohalophosphoric acid diester from solidifying. The method for adjusting the reaction starting temperature is not particularly limited. When the system is cooled to control so as to set the reaction starting temperature in the above-mentioned temperature range, control can be made by ice cooling of a reaction vessel including the monohalophosphoric acid diester and hydroxide charged therein. When the system is heated to control so as to set the reaction starting temperature in the above-mentioned temperature range, control can be made by an oil bath set at an arbitrary temperature. After completion of the reaction between the monohalophosphoric acid ester and the hydroxy compound, the temperature decreases to about room temperature.

It is also possible to produce the phosphoric acid triester by using a dihalophosphoric acid monoester represented by the following chemical formula (4) in place of the halophosphoric acid diester. Also in this case, reaction can be performed in the other organic solvent or in the absence of a solvent:

[Chemical Formula 13]

(4)

wherein R$^2$ is the same as defined in the chemical formula (1), and X represents I, Br, Cl or the like.

The use amount of the other organic solvent is preferably at least 2 times, more preferably 2 to 100 times, and still more preferably 2 to 50 times, the mass of the dihalophosphoric acid monoester. When the use amount of the other organic solvent is adjusted at at least 2 times the mass of the dihalophosphoric acid monoester, the reaction between the dihalophosphoric acid monoester and the hydroxy compound can be efficiently performed. The upper limit of the use amount of the other organic solvent is not particularly limited. However, the use of the organic solvent in an excessive amount requires energy more than necessary when this organic solvent is distilled off, thus resulting in an industrial disadvantage. It is therefore preferred to appropriately set the upper limit of the use amount of the organic solvent in accordance with the reactive species.

The use amount of the hydroxy compound is preferably in a range of 2 equivalents to 10 equivalents, more preferably 2 equivalents to 6 equivalents, and particularly preferably 2.05 equivalents to 3 equivalents, based on 1 equivalent of the dihalophosphoric acid monoester. When the use amount of the hydroxy compound is set at 2 equivalents or more, it is possible to prevent the dihalophosphoric acid monoester from remaining. The upper limit of the use amount of the hydroxy compound is not particularly limited. However, the use of the hydroxy compound in an amount of more than 10 equivalent requires energy more than necessary when the excess hydroxy compound is distilled off. It is therefore preferred to appropriately set the upper limit of the use amount of the hydroxy compound in accordance with the reactive species.

When the reaction between the dihalophosphoric acid monoester and the hydroxy compound is started, the numerical range of the reaction starting temperature is the same as in case where the monohalophosphoric acid diester is reacted with the hydroxy compound.

It is also possible to react a monohalophosphoric acid diester or a dihalophosphoric acid monoester with a hydroxy compound in the hydroxy compound in place of the other organic solvent in the presence of a base. In this case, the use amount of the hydroxy compound as the reaction solvent is the same as that of the other organic solvent. Examples of the base include, but are not limited to, triethylamine and the like.

The content of the base is preferably in a range of 1 equivalent to 5 equivalents, more preferably 1 equivalent to 3 equivalents, and still more preferably 1.05 equivalents to 2 equivalents, in the case of a monohalophosphoric acid diester. When the content of the base is set at 1 equivalent or more, it is possible to prevent the reactivity between the monohalophosphoric acid diester and the hydroxide from deteriorating and to suppress the unreacted monohalophosphoric acid diester or dihalophosphoric acid monoester from remaining, thus making it possible to suppress purity of the phosphoric acid triester from being lowered. Meanwhile, when the content of the base is set at 5 equivalent or more, it is possible to prevent consumption of energy required to remove excess base.

The content of the base is preferably in a range of 2 equivalents to 10 equivalents, more preferably 4 equivalents to 6 equivalents, and still more preferably 2.1 equivalents to 4 equivalents, in the case of a dihalophosphoric acid monoester. When the content of the base is set at 1 equivalent or more, it is possible to prevent the reactivity between the monohalophosphoric acid diester and the hydroxide from deteriorating and to suppress the unreacted monohalophosphoric acid diester or dihalophosphoric acid monoester from remaining, thus making it possible to suppress purity of the phosphoric acid triester from being lowered. Meanwhile, when the content of the base is set at 10 equivalents or more, it is possible to prevent consumption of energy required to remove excess base.

It is also possible to react a monohalophosphoric acid diester or a dihalophosphoric acid monoester with a hydroxy compound in the presence of a catalyst of a metal halide or in the absence of a catalyst. In this case, the reaction is preferably performed under reflux conditions. When the reaction is started, the reaction starting temperature is not particularly limited as long as the reaction proceeds. Usually, the reaction starting temperature is in a range of 40° C. or higher and 300° C. or lower, preferably 60° C. or higher and 250° C. or lower, and more preferably 80° C. or higher and lower than 200° C. When the reaction starting temperature is set at 40° C. or higher, the by-produced hydrogen halide can be efficiently removed. Meanwhile, when the reaction starting temperature is set at 300° C. or lower, excess energy used for the reaction can be suppressed. The method for adjusting the reaction starting temperature is not particularly limited. When the system is cooled to control so as to set the reaction starting temperature range in the above-mentioned temperature range, control can be made by ice cooling of a reaction vessel including the monohalophosphoric acid diester or dihalophosphoric acid monoester and the hydroxy compound charged therein. When the system is heated to control so as to set the reaction starting temperature in the above-mentioned temperature range, control can be made by an oil bath set at an arbitrary temperature. After completion of the reaction between the monohalophosphoric acid diester or dihalophosphoric acid monoester and the hydroxy compound, the temperature decreases to about room temperature.

The metal halide is not particularly limited and, for example, sodium chloride, magnesium chloride and the like can be used. When using the catalyst of the metal halide, the use amount of the metal halide is preferably in a range of 0.01 equivalent to 0.5 equivalent, more preferably 0.01 equivalent to 0.2 equivalent, and still more preferably 0.01 to 0.1 equivalent, based on the monohalophosphoric acid diester or dihalophosphoric acid monoester.

(Additive for Non-Aqueous Electrolytic Solution of Power Storage Element)

The phosphoric acid diester salt of the present embodiment can be used as an additive in a non-aqueous electrolytic solution for a power storage element. In this case, the non-aqueous electrolytic solution is configured by adding at least one phosphodiester salt, as an additive, to an organic solvent (non-aqueous solvent) containing an electrolyte dissolved therein.

In a sodium ion secondary battery as a sort of a power storage element, an irreversible reaction of decomposition of a non-aqueous electrolytic solution arises at an interface between electrodes and the non-aqueous electrolytic solution, at an initial time of charging the secondary battery. In accordance with the kind of electrode active materials, the kind of a non-aqueous solvent, an electrolyte and an additive in the non-aqueous electrolytic solution, and charge-discharge conditions, properties of a film to be formed, for example, thermal stability, ion conductivity, morphology, and denseness will significantly vary. Also in the present embodiment, a film is formed on each surface of electrode active materials by adding the phosphoric acid diester salt to the non-aqueous electrolytic solution as an additive. The effect of properties of this film, that is, thermal stability, film quality and the like can suppress charge-discharge characteristics of the sodium ion secondary from deteriorating and suppress the internal resistance from rising even after storage under high temperature environment (for example, 40° C. to 100° C.).

Regarding the sentence that the non-aqueous electrolytic solution for a power storage element of the present embodiment contains a "phosphoric acid diester salt as an additive", the phosphoric acid diester salt is used together with a main electrolyte in the non-aqueous electrolytic solution for a power storage element, and the additive means a compound which is added for the purpose of suppressing deterioration of charge-discharge characteristics of the power storage element, and suppressing the rise in internal resistance after storage at high temperature, leading to an improvement in battery characteristics.

The additive amount of the phosphodiester salt as the additive is preferably in a range of 0.005 to 5% by mass, more preferably 0.01 to 3% by mass, and still more preferably 0.15 to 1.5% by mass, based on the total mass of the non-aqueous electrolytic solution. When the additive amount is set at 0.005% by mass or more, it is possible to suppress charge-discharge characteristics from deteriorating and to suppress the rise in internal resistance even after exposing the secondary battery to high temperature environment. Meanwhile, when the additive amount is set at 5% by mass or less, it is possible to suppress the solubility of the electrolyte in the non-aqueous electrolytic solution from being lowered.

<Electrolyte>

It is possible to employ, as the above electrolyte, conventionally known electrolytes used in various power storage elements. When the electrolyte is for lithium ion batteries, the electrolyte may be a lithium salt. For example, when the power storage element is a sodium ion secondary battery, a sodium salt can be used.

The electrolyte is preferably an electrolyte which contains an anion containing fluorine. Specific examples of such a fluorine-containing anion include $BF_4^-$, $PF_6^-$, $BF_3CF_3^-$, $BF_3C_2F_5^-$, $CF_3SO_3^-$, $C_2F_5SO_3^-$, $C_3F_7SO_3^-$, $C_4F_9SO_3^-$, $N(SO_2F)_2^-$, $N(CF_3SO_2)_2^-$, $N(C_2F_5SO_2)_2^-$, $N(CF_3SO_2)(CF_3CO)^-$, $N(CF_3SO_2)(C_2F_5SO_2)^-$, $C(CF_3SO_2)_3^-$ and the like. These electrolytes can be used alone or in combination of two or more thereof. Among fluorine-containing anions, $BF_4^-$, $PF_6^-$, and $N(CF_3SO_2)_2^-$ are preferred, and $BF_4^-$, $PF_6^-$ are particularly preferred, from the viewpoint of improvement in safety/stability and electric conductivity of the non-aqueous electrolytic solution, and the cycle characteristics.

The concentration of the electrolyte in the organic solvent is not particularly limited, and is usually in a range of 0.1 to 2 M, preferably 0.15 to 1.8 M, more preferably 0.2 to 1.5 M, and particularly preferably 0.3 to 1.2 M. When the concentration is set at 0.1 M or more, it is possible to prevent the electric conductivity of the non-aqueous electrolytic solution from becoming insufficient. Meanwhile, when the concentration is set at 2 M or less, it is possible to suppress the electric conductivity from deteriorating due to the rise in viscosity of the non-aqueous electrolytic solution, thus making it possible to prevent secondary battery performance from deteriorating.

<Organic Solvent>

Examples of the organic solvent (non-aqueous solvent) used in the non-aqueous electrolytic solution include, but are not limited to, cyclic carbonate, chain carbonate, phosphate, cyclic ether, chain ether, lactone compound, chain ester, nitrile compound, amide compound, sulfone compound and the like. Among these organic solvents, carbonates are preferred from the viewpoint of being commonly used as an organic solvent for secondary batteries.

Examples of the cyclic carbonate include, but are not limited to, ethylene carbonate, propylene carbonate, butylene carbonate and the like. Among these, cyclic carbonates such as ethylene carbonate and propylene carbonate are preferred in view of improving the charge efficiency of the sodium ion secondary battery. Examples of the chain carbonate include, but are not limited to, dimethyl carbonate, ethylmethyl carbonate, diethyl carbonate and the like. Among these, dimethyl carbonate and ethylmethyl carbonate are preferred in view of improving the charge efficiency of the sodium ion secondary battery. Examples of the phosphate include, but are not limited to, trimethyl phosphate, triethyl phosphate, ethyldimethyl phosphate, diethylmethyl phosphate and the like. Examples of the cyclic ether include, but are not limited to, tetrahydrofuran, 2-methyltetrahydrofuran and the like. Examples of the chain ether include, but are not limited to dimethoxyethane. Examples of the lactone compound include, but are not limited to, γ-butyrolactone. Examples of the chain ester include, but are not limited to, methyl propionate, methyl acetate, ethyl acetate, methyl formate and the like. Examples of the nitrile compound include, but are not limited to, acetonitrile. Examples of the amide compound include, but are not limited to, dimethylformamide Examples of the sulfone compound include, but are not limited to, sulfolane, methylsulfolane and the like. It is also possible to suitably use those obtained by partially substituting hydrogens of a hydrocarbon group contained in the above organic solvent molecules with fluorine. These organic solvents may be used alone or in the form of a mixture of two or more thereof. From the viewpoint of availability and performances, carbonates are preferably used as the organic solvent.

<Method for Producing Non-Aqueous Electrolytic Solution>

The non-aqueous electrolytic solution of the present embodiment can be obtained by adding a salt of the above electrolyte to the above organic solvent (non-aqueous solvent) and adding a phosphoric acid diester salt as an additive. In this case, it is preferred to use, as the organic solvent, a salt of an electrolyte, phosphoric acid diester salt, and other additives to be added optionally, those in which impurities are reduced as much as possible by purifying in advance as long as the productivity of the non-aqueous electrolytic solution does not deteriorate.

<Others>

Conventionally known other additives may be added to the non-aqueous electrolytic solution according to the present embodiment.

(Electrolyte for Non-Aqueous Electrolytic Solution of Power Storage Element)

The phosphoric acid diester salt of the present embodiment can also be used as an electrolyte in a non-aqueous electrolytic solution of a power storage element. In this case, the non-aqueous electrolytic solution is configured by optionally including a known additive and a known electrolyte in an organic solvent (non-aqueous solvent) containing an electrolyte dissolved therein.

When using as the electrolyte, the concentration of the phosphoric acid diester salt in the organic solvent is not particularly limited, and is usually in a range of 0.1 to 2M, preferably 0.15 to 1.8M, more preferably 0.2 to 1.5M, and particularly preferably 0.3 to 1.2M. When the concentration is set at 0.1 M or more, it is possible to prevent the electric conductivity of the non-aqueous electrolytic solution from becoming insufficient and to suppress charge-discharge characteristics of the sodium ion secondary from deteriorating, and to suppress the internal resistance from rising even after storage under high temperature environment. Meanwhile, when the concentration is set at 2 M or less, it is possible to suppress the electric conductivity from deteriorating due to deterioration of the solubility in the non-aqueous electrolytic solution and the rise in viscosity of the non-aqueous electrolytic solution, thus making it possible to prevent the performance of the power storage element from deteriorating.

<Organic Solvent>

It is possible to use, as the organic solvent, organic solvents which are the same as those described in the case where the phosphoric acid diester salt of the present embodiment is used as an additive, without limitation.

<Production of Non-Aqueous Electrolytic Solution>

When using the phosphoric acid diester salt as an electrolyte, the non-aqueous electrolytic solution is obtained, for example, by adding a phosphoric acid diester salt to the above organic solvent (non-aqueous solvent) and optionally adding a known additive and a known electrolyte. In this case, it is preferred to use, as the organic solvent, a phosphoric acid diester salt, and other additives to be added optionally, those in which impurities are reduced as much as possible by purifying in advance as long as the productivity of the non-aqueous electrolytic solution does not deteriorate.
(Power Storage Element)

Examples of the power storage element of the present embodiment include a sodium ion secondary battery, a lithium ion secondary battery, an electric double layer capacitor and the like. The phosphoric acid diester salt of the present embodiment can be suitably used as an additive for a non-aqueous electrolytic solution and an electrolyte to these various power storage elements.

<Sodium Ion Secondary Battery>

When the power storage element is, for example, a sodium ion secondary battery, the following configuration can be employed. FIG. 1 is a schematic sectional view that schematically illustrates a sodium ion secondary battery with the above non-aqueous electrolytic solution.

As illustrated in FIG. 1, the sodium ion secondary battery according to the present embodiment has a structure in which in an internal space formed by a positive electrode can 4 and a negative electrode can 5, a stacked body is held and, in the stacked body, from the positive electrode can 4-side of the body, a positive electrode 1, a separator 3, a negative electrode 2, and a spacer 7 are stacked in this order. By interposing a spring 8 between the negative electrode can 5 and the separator 7, the positive electrode 1 and the negative electrode 2 can be pressed and bonded to each other in an appropriate degree to be fixed to each other. The positive electrode 1, the separator 3, and the negative electrode 2 are impregnated with the non-aqueous electrolytic solution, which contains a phosphoric acid diester salt, in the present embodiment. By putting the positive electrode can 4 and the negative electrode can 5 onto each other in the state of interposing a gasket 6 between the positive electrode can 4 and the negative electrode can 5, the both are bonded to each other so that the stacked body comes into an airtightly sealed state.

In the case of the sodium ion secondary battery, examples of the material of the positive electrode active material layer in the positive electrode 1 include, but are not limited to, a transition metal compound in which sodium ion has a diffusible structure, or an oxide of the transition metal compound and sodium. Specific examples thereof include $NaFeO_2$, $NaNiO_2$, $NaCoO_2$, $NaMnO_2$, $NaVO_2$, $NaCrO_2$, $Na_{0.7}(Mn_xNi_yCo_z)O_2$ (x+y+z=1, 0<x≤1, 0<y≤1, 0<z≤1), $Na_{2/3}(Ni_xMn_y)O_2$ (x+y=1, 0<x≤1, 0<y≤1), $Na_{2/3}(Fe_xMn_y)O_2$ (x+y=1, 0<x≤1, 0<y≤1), $Na_{2/3}(Ni_xMn_yMg_z)O_2$ (x+y+z=1, 0<x≤1, 0<y≤1, 0<z≤1), $Na_{2/3}(Ni_xMn_yAl_z)O_2$ (x+y+z=1, 0<x≤1, 0<y≤1, 0<z≤1), $Na_2Fe_2P_2O_7$, $Na_3V_2(PO_4)_3$, $Na_4Ni_3(PO_4)_2P_2O_7$, $Na_4Co_3(PO_4)_2P_2O_7$, $Na_2Fe_2(SO_4)_3$ and the like.

The positive electrode 1 can be obtained by press-molding the positive active materials listed up above together with a known conducting aid and a known binder, or by mixing the positive active material, together with a known conducting aid and a known binder, in an organic solvent such as pyrrolidone to prepare a paste, and applying the paste onto a current collector such as an aluminum foil, followed by drying.

In the case of a sodium ion battery, the material of a negative active material layer in the negative electrode 2 is not particularly limited as long as the material can store and release lithium. Examples thereof include metal sodium; metal oxide such as $Na_2Ti_6O_{13}$; and carbon materials such as natural graphite, artificial graphite, graphite boride, hard carbon, meso-carbon microbeads, pitch type carbon fiber, graphitized products, and carbon nanotubes.

The negative electrode 2 may be an electrode in the form of a foil or powder of the above electrode materials. In the case of the powdery negative electrode, this negative electrode can be obtained by press-molding the negative electrode material together with a known conducting aid and a known binder, or by mixing the material, together with a known conducting aid and a known binder, in an organic solvent such as pyrrolidone to prepare a paste, and applying the paste onto a current collector such as a copper foil, followed by drying.

In the sodium ion secondary battery according to the present embodiment, between the positive electrode 1 and the negative electrode 2, the separator 3 is usually interposed in order to prevent these electrodes from being short-circuited. The material and the shape of the separator 3 are not particularly limited. The material is preferably an electrically-insulating chemically-stable material through which the above-mentioned non-aqueous electrolytic solution is easy to pass. The separator 3 is, for example, a microporous film or sheet made of various polymeric materials. Specific examples of the polymeric material include nylon (registered trademark), nitrocellulose, polyacrylonitrile, polyvinylidene fluoride, and polyolefin polymers such as polyethylene and polypropylene. From the viewpoint of electrochemical stability and chemical stability, polyolefin polymers are preferred.

An optimal use voltage for the sodium ion secondary battery of the present embodiment varies in accordance with the combination of the positive electrode 1 with the negative electrode 2. Usually, the sodium ion secondary battery is usable at an average discharge voltage in a range of 2.4 to 4.5 V.

Examples of the form of the sodium ion secondary battery of the present embodiment include, but are not limited to, a cylindrical form, a rectangular form, a laminate form and the like, in addition to the coin-shaped cell illustrated in FIG. 1.

The sodium ion secondary battery according to the present embodiment can suppress deterioration of charge-discharge characteristics and the rise in internal resistance after storage in temperature load environment. Thus, the non-aqueous electrolytic solution of the present embodiment is suitably usable for sodium ion secondary batteries. The sodium ion secondary battery illustrated in FIG. 1 is an example, but the secondary battery of the invention is not limited thereto.

<Electric Double Layer Capacitor>

With respect to the case where the power storage element is an electric double layer capacitor, the same configuration as that of the sodium ion secondary battery can be employed. Specifically, an electric double layer capacitor can employ the structure in which, as illustrated in FIG. 1, in an internal space formed by a positive electrode can 4 and a negative electrode can 5, a stacked body is held and, in the stacked body, from the positive electrode can 4-side of the body, a positive electrode 1, a separator 3, a negative electrode 2, and a spacer 7 are stacked in this order. The positive electrode 1, the negative electrode 2, and the separator 3 are impregnated with the non-aqueous electrolytic solution containing a phosphoric acid diester salt of the present embodiment.

The positive electrode 1 and the negative electrode 2 can be obtained by press-molding the below-mentioned active carbon together with a known conducting aid and a known binder. The positive electrode 1 and the negative electrode 2 can also be obtained by mixing the positive active materials listed up above together with a known conducting aid and a known binder, in an organic solvent such as pyrrolidone to prepare a paste, and applying the paste onto a current collector such as an aluminum foil, followed by drying.

The active carbon is not particularly limited, and it is possible to use a known active carbon which is usually used. The specific surface area of the active carbon is not particularly limited, but is usually in a range of 1,000 $m^2/g$ to 3,000 $m^2/g$, and preferably 1,000 $m^2/g$ to 2,000 $m^2/g$.

Examples of the material of active carbon include, but are not limited to, carbonaceous raw materials such as lumber, coconut shell, sawdust, coal, pitch, coke, phenol resin, furan resin, polyvinyl chloride resin, polyvinylidene chloride resin, polyimide resin, polyamide resin, polycarbodiimide resin, waste plastic, and waste tire.

The active carbon is obtained by carbonizing the carbonaceous raw materials listed up above at a temperature of 900° C. or lower, followed by subjecting to an activation treatment. Examples of the activation method include, but are not limited to, a gas activation method, a chemical activation method and the like. In the case of the gas activation method, active carbon can be obtained by a catalytic reaction of a carbonated raw material with an oxidation gas such as water vapor, carbon dioxide, or oxygen at high temperature in a range of 600° C. to 1,000° C. In the case of the chemical activation method, active carbon can be obtained by mixing a carbonized raw material with a chemical such as zinc chloride, phosphoric acid, sodium phosphate, calcium chloride, potassium sulfide, potassium hydroxide, sodium hydroxide, potassium carbonate, sodium carbonate, sodium sulfate, potassium sulfate, calcium carbonate, boric acid, or nitric acid, and heating to arbitrary temperature in an inert atmosphere to thereby perform a dehydration/oxidation reaction of the chemical. By performing these activation treatments, active carbon formed with numerous pores can be obtained, thus making it possible to increase a specific surface area thereof.

EXAMPLES

Preferred examples of the present invention will be illustratively described in detail below. However, about materials, mixing amounts and others mentioned in the Examples, the scope of the present invention is not limited only to these described matters unless the specification especially includes a restrictive description thereabout.

Example 1

Synthesis of ethyl bis(2,2,2-trifluoroethyl)phosphate

In a 200 mL beaker, 15 g of 2,2,2-trifluoroethanol, 14 g of triethylamine, and 100 g of dimethoxyethane were charged. While stirring, a solution prepared by diluting 10 g of ethyl dichlorophosphate to 50% with 10 g of dimethoxyethane was slowly added dropwise at room temperature. It was verified that heat is gradually generated during dropwise addition, and a white precipitate is precipitated in the system. Thereafter, stirring was performed at room temperature for 1 hour. The white precipitate was then separated into a white solid and a filtrate by performing filtration under reduced pressure. Thereafter, dimethoxyethane was distilled off from the filtrate under reduced pressure. Subsequently, the thus obtained liquid was repeatedly washed three times by adding water, and the liquid in the lower layer was isolated to obtain 14 g of ethyl bis(2,2,2-trifluoroethyl) phosphate as a colorless transparent liquid.

Synthesis of sodium ethyl(2,2,2-trifluoroethyl)phosphate

In a 50 mL recovery flask, 4.2 g of the ethyl bis(2,2,2-trifluoroethyl)phosphate was charged and then an aqueous sodium hydroxide solution was charged. The aqueous sodium hydroxide solution is prepared by dissolving 0.56 g of sodium hydroxide in 5.0 g of water. Thereafter, while stirring, the mixture was heated under reflux at 100° C. to 110° C. for 1 hour. The solvent was distilled off under reduced pressure at 80° C. to obtain 2.6 g of a white solid.

The thus obtained white solid was subjected to anion analysis using ion chromatography <IC-850, manufactured by Metrohm AG>. As a result, one novel peak was detected. Thus, it was verified that novel anions are produced. Furthermore, the thus obtained white solid was subjected to negative ion analysis using LC/MS (manufactured by Waters Corporation). As a result, a mass peak was observed at m/z=207.1. Since this approximately corresponds with the molecular weight of ethyl(2,2,2-trifluoroethyl)phosphoric acid anion, it was verified that the thus obtained white solid is sodium ethyl(2,2,2-trifluoroethyl)phosphate. The m/z means a mass-to-charge ratio, m represents the mass of ions, and z represents the charge number of ions.

<Preparation of Non-Aqueous Electrolytic Solution for Sodium Ion Secondary Batteries>

Inside a dry box having an argon atmosphere having a dew point of −70° C. or lower, a non-aqueous electrolytic solution was prepared to set the concentration of $NaPF_6$ at 1.0 mol/liter in propylene carbonate (PC) (sodium battery grade, manufactured by Kishida Chemical Co., Ltd.). Furthermore, a preparation was made to set the addition amount of the sodium ethyl(2,2,2-trifluoroethyl)phosphate at 0.5% by mass of the whole mass of the non-aqueous electrolytic solution. In this way, a non-aqueous electrolytic solution for sodium ion secondary batteries, which contains sodium ethyl(2,2,2-trifluoroethyl)phosphate as an additive, of the present example was prepared.

Example 2

Synthesis of ethyl bis(2,2,2-trifluoroethyl)phosphate

In the same manner as in Example 1, ethyl bis(2,2,2-trifluoroethyl)phosphate was synthesized.

Synthesis of potassium ethyl(2,2,2-trifluoroethyl)phosphate

In a 50 mL recovery flask, 10.0 g of the ethyl bis(2,2,2-trifluoroethyl)phosphate was charged and then an aqueous solution prepared by dissolving 1.8 g of potassium hydroxide in 5.0 g of water was charged. Thereafter, while stirring, the mixture was heated under reflux at 100° C. to 110° C. for 1 hour. The solvent was distilled off under reduced pressure at 80° C. to obtain 7.2 g of a white solid.

The thus obtained white solid was subjected to anion analysis using ion chromatography <IC-850, manufactured by Metrohm AG>. As a result, one novel peak was detected at the same detection time as that of the sodium ethyl(2,2,2-trifluoroethyl)phosphate. Thus, it was verified that the thus produced novel anion is ethyl(2,2,2-trifluoroethyl)phosphoric acid anion, and the thus obtained white solid is potassium ethyl(2,2,2-trifluoroethyl)phosphate.

Example 3

Synthesis of ethyl(2,2,2-trifluoroethyl)phosphoric acid

In a 50 mL recovery flask, 4.0 g of potassium ethyl(2,2,2-trifluoroethyl)phosphate synthesized in Example 2 was charged and then hydrochloric acid was charged. The charged hydrochloric acid is prepared by mixing 2.7 g of hydrochloric acid having the concentration of 37% with 10.0 g of water. Thereafter, stirring was performed at room temperature for 15 minutes. Subsequently, solvent extraction was performed using 25 mL of diethyl ether as an extraction solvent. The solvent extraction was performed four times. Thereafter, diethyl ether was distilled off under reduced pressure at 40° C. to obtain 3.3 g of a colorless transparent liquid.

The thus obtained colorless transparent liquid was subjected to anion analysis using ion chromatography <IC-850, manufactured by Metrohm AG>. As a result, one novel peak was detected at the same detection time as that of the sodium ethyl(2,2,2-trifluoroethyl)phosphate. Thus, it was verified that the thus produced novel anion is ethyl(2,2,2-trifluoroethyl)phosphoric acid anion, and the thus obtained colorless transparent liquid is ethyl(2,2,2-trifluoroethyl)phosphoric acid.

Example 4

Synthesis of ethyl bis(2,2,2-trifluoroethyl)phosphate

In the same manner as in Example 1, ethyl bis(2,2,2-trifluoroethyl)phosphate was synthesized.

Synthesis of calcium ethyl(2,2,2-trifluoroethyl)phosphate

In a 50 mL recovery flask, 1.0 g of the ethyl bis(2,2,2-trifluoroethyl)phosphate was charged and then an aqueous calcium hydroxide solution was charged. The aqueous sodium hydroxide solution is composed of a suspension prepared by adding 10.0 g of water to 0.1 g of calcium hydroxide. Thereafter, while stirring, the mixture was heated under reflux at 100° C. to 110° C. for 2 hours. Furthermore, the solvent was distilled off under reduced pressure at 80° C. to obtain 0.6 g of a white solid.

The thus obtained white solid was subjected to anion analysis using ion chromatography <IC-850, manufactured by Metrohm AG>. As a result, one novel peak was detected at the same detection time as that of the sodium ethyl(2,2,2-trifluoroethyl)phosphate. Thus, it was verified that the thus produced novel anion is ethyl(2,2,2-trifluoroethyl)phosphoric acid anion, and the thus obtained white solid is calcium ethyl(2,2,2-trifluoroethyl)phosphate.

Example 5

Synthesis of ethyl bis(2,2,2-trifluoroethyl)phosphate

In the same manner as in Example 1, ethyl bis(2,2,2-trifluoroethyl)phosphate was synthesized.

Synthesis of magnesium ethyl(2,2,2-trifluoroethyl)phosphate

In a 50 mL recovery flask, 6.0 g of the ethyl bis(2,2,2-trifluoroethyl)phosphate was charged and then an aqueous magnesium hydroxide solution was charged. The aqueous magnesium hydroxide solution is composed of a suspension prepared by adding 15.0 g of water to 0.6 g of magnesium hydroxide. Thereafter, while stirring, the mixture was heated under reflux at 100° C. to 110° C. for 10 hours. Furthermore, the solvent was distilled off under reduced pressure at 80° C. to obtain 4.2 g of a white solid.

The thus obtained white solid was subjected to anion analysis using ion chromatography <IC-850, manufactured by Metrohm AG>. As a result, one novel peak was detected at the same detection time as that of the sodium ethyl(2,2,2-trifluoroethyl)phosphate. Thus, it was verified that the thus produced novel anion is ethyl(2,2,2-trifluoroethyl)phosphoric acid anion, and the thus obtained white solid is magnesium ethyl(2,2,2-trifluoroethyl)phosphate.

Example 6

Synthesis of ethyl bis(2-(2-(2-methoxyethoxy)ethoxy))phosphate

In a 200 mL beaker, 20.6 g of triethylene glycol monomethyl ether, 12.4 g of triethylamine, and 100 g of dimethoxyethane were charged. While stirring, a solution prepared by diluting 10 g of ethyl dichlorophosphate to 50% with 10 g of dimethoxyethane was slowly added dropwise at room temperature. It was verified that heat is gradually generated during dropwise addition, and a white precipitate is precipitated in the system. Thereafter, stirring was performed at room temperature for 1 hour. The white precipitate was then separated into a white solid and a filtrate by performing filtration under reduced pressure. Thereafter, dimethoxyethane was distilled off from the filtrate under reduced pressure. Subsequently, the thus obtained liquid was dissolved by adding dimethoxyethane, and purified by subjecting to flash chromatography using a silica gel to obtain 20.5 g of ethyl bis(2-(2-(2-methoxyethoxy)ethoxy))phosphate as a colorless transparent liquid.

Synthesis of sodium ethyl(2-(2-(2-methoxyethoxy)ethoxy))phosphate

In a 50 mL recovery flask, 10 g of the ethyl bis(2-(2-(2-methoxyethoxy)ethoxy))phosphate was charged and then an aqueous sodium hydroxide solution was charged. The aqueous sodium hydroxide solution is prepared by dissolving 0.91 g of sodium hydroxide in 10 g of water. Thereafter, while stirring, the mixture was heated under reflux at 100° C. to 110° C. for 1 hour. Furthermore, the solvent was distilled off under reduced pressure at 80° C. to obtain 6.7 g of a white gel-like solid.

The thus obtained white solid was subjected to anion analysis using ion chromatography <IC-850, manufactured by Metrohm AG>. As a result, one novel peak was detected. Thus, it was verified that novel anions are produced. Furthermore, the thus obtained white solid was subjected to negative ion analysis using LC/MS (manufactured by Waters Corporation). As a result, a mass peak was observed at m/z=271.1. Since this approximately corresponds with the molecular weight of ethyl(2-(2-(2-methoxyethoxy)ethoxy)) phosphoric acid anion, it was verified that the thus obtained white solid is sodium ethyl(2-(2-(2-methoxyethoxy)ethoxy))phosphate.

<Preparation of Non-Aqueous Electrolytic Solution for Sodium Ion Secondary Batteries>

In the same manner as in Example 1, a non-aqueous electrolytic solution for sodium ion secondary batteries according to the present example was prepared.

Example 7

Synthesis of ethyl bis(2,2,2-trifluoroethyl)phosphate

In the same manner as in Example 1, ethyl bis(2,2,2-trifluoroethyl)phosphate was synthesized.

Synthesis of 1-ethyl-3-methylimidazoliumethyl(2,2,2-trifluoroethyl)phosphoric acid In a 200 mL recovery flask, 20.0 g of the ethyl bis(2,2,2-trifluoroethyl)phosphate was charged and then 83.9 g of an aqueous 10% 1-ethyl-3-methylimidazolium hydroxide solution was charged. Thereafter, while stirring, the mixture was heated under reflux at 100° C. to 110° C. for 1 hour. Furthermore, the solvent was distilled off under reduced pressure at 80° C. to obtain 19.5 g of an oily pale yellow transparent liquid.

The thus obtained white solid was subjected to anion analysis using ion chromatography <IC-850, manufactured by Metrohm AG>. As a result, one novel peak was detected at the same detection time as that of the sodium ethyl(2,2,2-trifluoroethyl)phosphate. Thus, it was verified that the thus produced novel anion is ethyl(2,2,2-trifluoroethyl)phosphoric acid anion, and the thus obtained white solid is 1-ethyl-3-methylimidazoliumethyl(2,2,2-trifluoroethyl)phosphoric acid.

Example 8

Synthesis of Ethyl Bishexafluoroisopropyl Phosphate

In a 200 mL beaker, 9.9 g of hexafluoroisopropyl alcohol, 5.5 g of triethylamine, and 100 g of dimethoxyethane were charged. While stirring, 4.0 g of ethyl dichlorophosphate was slowly added dropwise at room temperature. It was verified that heat is gradually generated during dropwise addition, and a white precipitate is precipitated in the system. Thereafter, stirring was performed at room temperature for 1 hour. The white precipitate was then separated into a white solid and a filtrate by performing filtration under reduced pressure. Thereafter, dimethoxyethane was distilled off from the filtrate under reduced pressure. Subsequently, the thus obtained liquid was repeatedly washed three times by adding water, and the liquid in the lower layer was isolated to obtain 9.1 g of ethyl bis(1,1,1,3,3,3-hexafluoroisopropyl)phosphate as a colorless transparent liquid.

<Synthesis of Sodium Ethyl Hexafluoroisopropyl Phosphate>

In a 50 mL recovery flask, 5.0 g of the ethyl bishexafluoroisopropyl phosphate was charged and then an aqueous sodium hydroxide solution was charged. The aqueous sodium hydroxide solution is prepared by dissolving 0.46 g of sodium hydroxide in 5.0 g of water. Thereafter, while stirring, the mixture was heated under reflux at 100° C. to 110° C. for 1 hour. Furthermore, the solvent was distilled off under reduced pressure at 80° C. to obtain 2.5 g of a white solid.

The thus obtained white solid was subjected to anion analysis using ion chromatography <IC-850, manufactured by Metrohm AG>. As a result, one novel peak was detected. Thus, it was verified that novel anions are produced. Furthermore, the thus obtained white solid was subjected to negative ion analysis using LC/MS (manufactured by Waters Corporation). As a result, a mass peak was observed at m/z=274.9. Since this approximately corresponds with the molecular weight of ethylhexafluoroisopropylphosphoric acid anion, it was verified that the thus obtained white solid is sodium ethyl hexafluoroisopropyl phosphate.

<Preparation of Non-Aqueous Electrolytic Solution for Sodium Ion Secondary Batteries>

In the same manner as in Example 1, a non-aqueous electrolytic solution for sodium ion secondary batteries according to the present example was prepared.

Example 9

Synthesis of Ethyl Dimethyl Phosphate

In a 500 mL beaker, 7.4 g of methanol, 20.5 g of triethylamine, and 200 g of dimethoxyethane were charged. While stirring, 15.0 g of ethyl dichlorophosphate was slowly added dropwise at room temperature. It was verified that heat is gradually generated during dropwise addition, and a white precipitate is precipitated in the system. Thereafter, stirring was performed at room temperature for 1 hour. The white precipitate was then separated into a white solid and a filtrate by performing filtration under reduced pressure. Thereafter, dimethoxyethane was distilled off from the filtrate under reduced pressure. Subsequently, the thus obtained liquid was dissolved by adding ethyl acetate, and purified by subjecting to flash chromatography using ethyl acetate and a silica gel to obtain 10.0 g of ethyl dimethyl phosphate as a colorless transparent liquid.

<Synthesis of Sodium Ethyl Methyl Phosphate>

In a 50 mL recovery flask, 4.0 g of the ethyl dimethyl phosphate was charged and then an aqueous sodium hydroxide solution was charged. The aqueous sodium hydroxide solution is prepared by dissolving 1.0 g of sodium hydroxide in 5.0 g of water. Thereafter, while stirring, the mixture was heated under reflux at 100° C. to 110° C. for 1 hour. Furthermore, the solvent was distilled off under reduced pressure at 80° C. to obtain 3.8 g of a white solid.

The thus obtained white solid was subjected to anion analysis using ion chromatography <IC-850, manufactured by Metrohm AG>. As a result, one novel peak was detected. Thus, it was verified that novel anions are produced. Furthermore, the thus obtained white solid was subjected to negative ion analysis using LC/MS (manufactured by Waters Corporation). As a result, a mass peak was observed at m/z=138.9. Since this approximately corresponds with the molecular weight of ethylmethylphosphoric acid anion, it was verified that the thus obtained white solid is sodium ethyl dimethyl phosphate.

<Preparation of Non-Aqueous Electrolytic Solution for Sodium Ion Secondary Batteries>

In the same manner as in Example 1, a non-aqueous electrolytic solution for sodium ion secondary batteries according to the present example was prepared.

Example 10

<Synthesis of Lithium Ethyl Methyl Phosphate>

In a 50 mL recovery flask, 5.0 g of the ethyl dimethyl phosphate was charged and then an aqueous solution prepared by dissolving 1.3 g of lithium hydroxide monohydrate in 15.0 g of water was charged. Thereafter, while stirring, the mixture was heated under reflux at 100° C. to 110° C. for 1 hour. Furthermore, the solvent was distilled off under reduced pressure at 80° C. to obtain 3.0 g of a white solid.

The thus obtained white solid was subjected to anion analysis using ion chromatography <IC-850, manufactured by Metrohm AG>. As a result, one novel peak was detected. Thus, it was verified that novel anions are produced. Furthermore, the thus obtained white solid was subjected to negative ion analysis using LC/MS (manufactured by Waters Corporation). As a result, a mass peak was observed at m/z=138.9. Since this approximately corresponds with the molecular weight of ethyldimethylphosphoric acid anion, it was verified that the thus obtained white solid is lithium ethyl dimethyl phosphate.

Example 11

In the present example, the addition amount of sodium ethyl(2,2,2-trifluoroethyl)phosphate of Example 1 was changed to 0.1% by mass based on the total mass of the non-aqueous electrolytic solution. In the same manner as in Example 1, except for the others, a non-aqueous electrolytic solution for sodium ion secondary batteries was prepared.

Example 12

In the present example, the addition amount of sodium ethyl(2,2,2-trifluoroethyl)phosphate of Example 1 was changed to 5.0% by mass based on the total mass of the non-aqueous electrolytic solution. In the same manner as in Example 1, except for the others, a non-aqueous electrolytic solution for sodium ion secondary batteries was prepared.

Example 13

In the present example, the addition amount of ethyl(2,2,2-trifluoroethyl)phosphoric acid of Example 3 was changed to 0.1% by mass based on the total mass of the non-aqueous electrolytic solution. In the same manner as in Example 3, except for the others, a non-aqueous electrolytic solution for sodium ion secondary batteries was prepared.

Example 14

Synthesis of ethyl bis(2,2,2-trifluoroethyl)phosphate

In the same manner as in Example 1, ethyl bis(2,2,2-trifluoroethyl)phosphate was synthesized.

Synthesis of sodium ethyl(2,2,2-trifluoroethyl)phosphate

In a 50 mL recovery flask, 5.0 g of the ethyl bis(2,2,2-trifluoroethyl)phosphate was charged and then an aqueous sodium hydroxide solution was charged. The aqueous sodium hydroxide solution is prepared by dissolving 0.3 g of sodium hydroxide in 5.0 g of water. Thereafter, while stirring, the mixture was heated under reflux at 100° C. to 110° C. for 1 hour. Furthermore, the solvent was distilled off under reduced pressure at 80° C. to obtain a white solid. Subsequently, the thus obtained white solid was suspended in 10.0 g of dimethyl carbonate, followed by filtration to obtain 1.6 g of a white solid.

The thus obtained white solid was subjected to anion analysis using ion chromatography <IC-850, manufactured by Metrohm AG>. As a result, one novel peak was detected at the same detection time as that of the sodium ethyl(2,2,2-trifluoroethyl)phosphate. Thus, it was verified that the thus produced novel anion is ethyl(2,2,2-trifluoroethyl)phosphoric acid anion, and the thus obtained white solid is sodium ethyl(2,2,2-trifluoroethyl)phosphate.

<Preparation of Non-Aqueous Electrolytic Solution for Sodium Ion Secondary Batteries>

In the same manner as in Example 1, a non-aqueous electrolytic solution for sodium ion secondary batteries according to the present example was prepared.

Example 15

Synthesis of ethyl bis(2,2,2-trifluoroethyl)phosphate

In the same manner as in Example 1, ethyl bis(2,2,2-trifluoroethyl)phosphate was synthesized.

Synthesis of sodium ethyl(2,2,2-trifluoroethyl)phosphate

In a 50 mL recovery flask, 5.0 g of the ethyl bis(2,2,2-trifluoroethyl)phosphate was charged and then an aqueous solution prepared by dissolving 0.7 g of sodium hydroxide in 5.0 g of water was charged. Thereafter, while stirring, the mixture was heated under reflux at 100° C. to 110° C. for 1 hour. Furthermore, the solvent was distilled off under reduced pressure at 80° C. to obtain 3.9 g of a white solid.

The thus obtained white solid was subjected to anion analysis using ion chromatography <IC-850, manufactured by Metrohm AG>. As a result, one novel peak was detected at the same detection time as that of the sodium ethyl(2,2,2-trifluoroethyl)phosphate. Thus, it was verified that the thus produced novel anion is ethyl(2,2,2-trifluoroethyl)phosphoric acid anion, and the thus obtained white solid is sodium ethyl(2,2,2-trifluoroethyl)phosphate.

<Preparation Non-Aqueous Electrolytic Solution for Sodium Ion Secondary Batteries>

In the same manner as in Example 1, a non-aqueous electrolytic solution for sodium ion secondary batteries according to the present example was prepared.

Example 16

Synthesis of ethyl bis(2,2,2-trifluoroethyl)phosphate

In the same manner as in Example 1, ethyl bis(2,2,2-trifluoroethyl)phosphate was synthesized.

Synthesis of sodium ethyl(2,2,2-trifluoroethyl)phosphate

In a 50 mL recovery flask, 5.0 g of the ethyl bis(2,2,2-trifluoroethyl)phosphate was charged and then 30.0 g of dimethoxyethane was charged as a reaction solvent. Thereafter, an aqueous solution prepared by dissolving 0.7 g of sodium hydroxide in 1.2 g of water was charged. Thereafter, while stirring, the mixture was heated under reflux at 100° C. to 110° C. for 1 hour. Furthermore, the solvent was distilled off under reduced pressure at 80° C. to obtain 3.9 g of a white solid.

The thus obtained white solid was subjected to anion analysis using ion chromatography <IC-850, manufactured by Metrohm AG>. As a result, one novel peak was detected at the same detection time as that of the sodium ethyl(2,2,2-trifluoroethyl)phosphate. Thus, it was verified that the thus produced novel anion is ethyl(2,2,2-trifluoroethyl)phosphoric acid anion, and the thus obtained white solid is sodium ethyl(2,2,2-trifluoroethyl)phosphate.
<Preparation of Non-Aqueous Electrolytic Solution for Sodium Ion Secondary Batteries>
In the same manner as in Example 1, a non-aqueous electrolytic solution for sodium ion secondary batteries according to the present example was prepared.

Example 17

Synthesis of ethyl bis(2,2,2-trifluoroethyl)phosphate

In the same manner as in Example 1, ethyl bis(2,2,2-trifluoroethyl)phosphate was synthesized.

Synthesis of sodium ethyl(2,2,2-trifluoroethyl)phosphate

In a 50 mL recovery flask, 20.0 g of the ethyl bis(2,2,2-trifluoroethyl)phosphate was charged and then an aqueous solution prepared by dissolving 0.6 g of sodium hydroxide in 1.2 g of water was charged. Thereafter, while stirring, the mixture was heated under reflux at 100° C. to 110° C. for 1 hour. Furthermore, the solvent and the solid were filtered to obtain a white solid. The solvent was distilled off from the thus obtained white solid under reduced pressure at 80° C. to obtain 2.2 g of a white solid.
The thus obtained white solid was subjected to anion analysis using ion chromatography <IC-850, manufactured by Metrohm AG>. As a result, one novel peak was detected at the same detection time as that of the sodium ethyl(2,2,2-trifluoroethyl)phosphate. Thus, it was verified that the thus produced novel anion is ethyl(2,2,2-trifluoroethyl)phosphoric acid anion, and the thus obtained white solid is sodium ethyl(2,2,2-trifluoroethyl)phosphate.
<Preparation of Non-Aqueous Electrolytic Solution for Sodium Ion Secondary Batteries>
In the same manner as in Example 1, a non-aqueous electrolytic solution for sodium ion secondary batteries according to the present example was prepared.

Comparative Example 1

In the same manner as in Example 1, except that sodium ethyl(2,2,2-trifluoroethyl)phosphate of Example 1 was not added in the present comparative example, a non-aqueous electrolytic solution for sodium ion secondary batteries was prepared.
(Evaluation of Electrochemical Characteristics of Sodium Ion Secondary Battery)
Electrochemical characteristics of sodium ion secondary batteries using each of non-aqueous electrolytic solutions of Examples 1, 6, 8, 9, and 11 to 17 and Comparative Example 1 were evaluated. In the evaluation, a three-electrode type evaluation cell illustrated in FIG. 2 was used.

Figure 2:
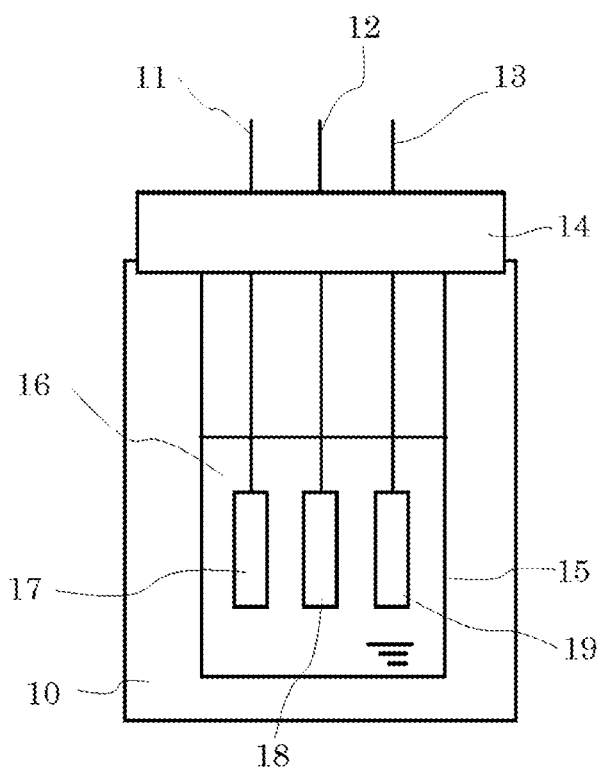
FIG. 2 is a schematic sectional view which schematically illustrates an electrochemical characteristics evaluation cell with a non-aqueous electrolytic solution containing an additive for a non-aqueous electrolytic solution of the present invention added therein.

<Assembling of Sodium Ion Secondary Battery>
A glass container 15 with a Teflon (registered trademark) lid 14 in the evaluation cell illustrated in FIG. 2 was filled with each of the non-aqueous electrolytic solutions obtained in Examples and Comparative Example 1. A working electrode 17 was supported by a stainless steel supporting rod 11 for a working electrode; a reference electrode 18 was supported by a stainless steel supporting rod 12 for a reference electrode; and a counter electrode 19 was supported by a stainless steel supporting rod 13 for a counter electrode.
The following electrodes were used as the working electrode 17. That is, an electrode, which is obtained by making $NaCrO_2$ together with an active material, a conducting aid and a binder into a paste form, applying the paste onto a current collector made of an aluminum foil, drying the paste, making the dried paste into a sheet form, and then cutting out the sheet into a 1-cm square piece, was used as a working electrode 17. Regarding the reference electrode 18 and the counter electrode 19, a sodium foil was used notwithstanding whether the positive or negative electrode material was to be evaluated.
The stainless steel supporting rod 11 for the working electrode, the stainless steel supporting rod 12 for the reference electrode, and the stainless steel supporting rod 13 for the counter electrode were fixed through the Teflon lid 14. The Teflon lid was fitted to the glass container 15 in which a non-aqueous electrolytic solution 16 was added. Simultaneously, the working electrode 17, the reference electrode 18 and the counter electrode 19 were simultaneously immersed in the non-aqueous electrolytic solution 16.
The glass container 15 was inserted and fitted into an aluminum block 10, the temperature of the block 10 being controllable, to adjust the temperature of the inside of the glass container 15.
As an electrochemical measuring instrument, PGSTAT302N manufactured by Metrohm Autolab was used to carry out cyclic voltammetry measurements and AC impedance measurements. All operations from assembling of the evaluation cell to the measurements were made in the argon glove box, which had a dew point of −70° C. or lower.
<Evaluation of Positive Electrode Material of Sodium Ion Secondary Battery>
After the temperature of the non-aqueous electrolytic solution was kept at 25° C., the cyclic voltammetry measurements were performed at a sweep rate of 1 mV/second from the immersion potential to 3,400 mV. The discharge capacity in the 5th cycle when using the non-aqueous electrolytic solution of Comparative Example 1 was regarded as 100, and the ratio of the charge capacity in the 5th cycle when using each of the non-aqueous electrolytic solutions of Examples 1, 6, 8, 9, and 11 to 17 is shown in Table 1 below.

TABLE 1

| | Non-aqueous electrolytic solution | | Addition amount of additive (% by mass) | Discharge capacity ratio at 25° C. after 5 cycles |
|---|---|---|---|---|
| | Electrolyte | Additive | | |
| Example 1 | $NaPF_6$ | Sodium ethyl(2,2,2-trifluoroethyl)phosphate | 0.5 | 120 |
| Example 6 | $NaPF_6$ | Sodium ethyl(2-(2-(2-methoxyethoxy)ethoxy))phosphate | 0.5 | 115 |
| Example 8 | $NaPF_6$ | Sodium ethyl hexafluoroisopropyl phosphate | 0.5 | 113 |
| Example 9 | $NaPF_6$ | Sodium ethyl methyl phosphate | 0.5 | 116 |

TABLE 1-continued

| | Non-aqueous electrolytic solution | | Addition amount of additive (% by mass) | Discharge capacity ratio at 25° C. after 5 cycles |
|---|---|---|---|---|
| | Electrolyte | Additive | | |
| Example 11 | NaPF$_6$ | Sodium ethyl(2,2,2-trifluoroethyl)phosphate | 0.1 | 115 |
| Example 12 | NaPF$_6$ | Sodium ethyl(2,2,2-trifluoroethyl)phosphate | 5.0 | 124 |
| Example 13 | NaPF$_6$ | ethyl(2,2,2-trifluoroethyl)phosphoric acid | 0.1 | 111 |
| Example 14 | NaPF$_6$ | Sodium ethyl(2,2,2-trifluoroethyl)phosphate | 0.5 | 120 |
| Example 15 | NaPF$_6$ | Sodium ethyl(2,2,2-trifluoroethyl)phosphate | 0.5 | 121 |
| Example 16 | NaPF$_6$ | Sodium ethyl(2,2,2-trifluoroethyl)phosphate | 0.5 | 121 |
| Example 17 | NaPF$_6$ | Sodium ethyl(2,2,2-trifluoroethyl)phosphate | 0.5 | 120 |
| Comparative Example 1 | NaPF$_6$ | — | — | 100 |

<Evaluation of Positive Electrode Internal Resistance of Sodium Ion Secondary Battery>

Subsequently, while the temperature of the non-aqueous electrolytic solution was kept at 25° C., the battery was charged to 3,400 mV at a charge current of 0.7 mA. Thereafter, the battery was kept at 3,400 mV for 3 hours. Thereafter, while the application of the voltage of 3,400 mV was kept as it was, the temperature was raised to 60° C., followed by keeping at 60° C. for 5 hours. Thereafter, the temperature was lowered to 0° C. step by step, and the AC impedance was measured, followed by comparison and evaluation about the electrode resistance. The resistance at 0° C. when using the non-aqueous electrolytic solution of Comparative Example 1 was regarded as 100, and the ratio of the internal resistance of the positive electrode in each non-aqueous electrolytic solution of Example 1 is shown in Table 2 below.

was charged. Thereafter, while stirring, the mixture was heated under reflux at 100° C. to 110° C. for 1 hour. The solvent was distilled off under reduced pressure at 80° C. to obtain 20.8 g of an oily colorless transparent liquid.

The thus obtained white solid was subjected to anion analysis using ion chromatography <IC-850, manufactured by Metrohm AG>. As a result, one novel peak was detected at the same detection time as that of the sodium ethyl(2,2,2-trifluoroethyl)phosphate. Thus, it was verified that the thus produced novel anion is ethyl(2,2,2-trifluoroethyl)phosphoric acid anion, and the thus obtained white solid is triethylmethylammonium ethyl(2,2,2-trifluoroethyl)phosphoric acid.

<Preparation of Non-Aqueous Electrolytic Solution for Electric Double Layer Capacitor>

Inside a dry box having an argon atmosphere having a dew point of −70° C. or lower, a non-aqueous electrolytic

TABLE 2

| | Non-aqueous electrolytic solution | | Internal resistance ratio at 60° C. after 5 hours |
|---|---|---|---|
| | Electrolyte | Additive | |
| Example 1 | NaPF$_6$ | Sodium ethyl(2,2,2-trifluoroethyl)phosphate | 72 |
| Example 6 | NaPF$_6$ | Sodium ethyl(2-(2-(2-methoxyethoxy)ethoxy))phosphate | 87 |
| Example 8 | NaPF$_6$ | Sodium ethyl hexafluoroisopropyl phosphate | 91 |
| Example 9 | NaPF$_6$ | Sodium ethyl methyl phosphate | 88 |
| Example 11 | NaPF$_6$ | Sodium ethyl(2,2,2-trifluoroethyl)phosphate | 90 |
| Example 12 | NaPF$_6$ | Sodium ethyl(2,2,2-trifluoroethyl)phosphate | 74 |
| Example 13 | NaPF$_6$ | ethyl(2,2,2-trifluoroethyl)phosphoric acid | 92 |
| Example 14 | NaPF$_6$ | Sodium ethyl(2,2,2-trifluoroethyl)phosphate | 73 |
| Example 15 | NaPF$_6$ | Sodium ethyl(2,2,2-trifluoroethyl)phosphate | 70 |
| Example 16 | NaPF$_6$ | Sodium ethyl(2,2,2-trifluoroethyl)phosphate | 69 |
| Example 17 | NaPF$_6$ | Sodium ethyl(2,2,2-trifluoroethyl)phosphate | 71 |
| Comparative Example 1 | NaPF$_6$ | — | 100 |

Example 18

Synthesis of ethyl bis(2,2,2-trifluoroethyl)phosphate

In the same manner as in Example 1, ethyl bis(2,2,2-trifluoroethyl)phosphate was synthesized.

Synthesis of triethylmethylammonium ethyl(2,2,2-trifluoroethyl)phosphoric acid

In a 100 mL recovery flask, 20.0 g of the ethyl bis(2,2,2-trifluoroethyl)phosphate was charged and then 24.9 g of an aqueous 35% triethylmethylammonium hydroxide solution solution was prepared to set the concentration of triethylmethylammonium ethyl(2,2,2-trifluoroethyl)phosphoric acid synthesized in Example 5 at 1.0 mol/liter in propylene carbonate (PC) (sodium battery grade, manufactured by Kishida Chemical Co., Ltd.). Thus, a non-aqueous electrolytic solution for electric double layer capacitors, which contains triethylmethylammonium ethyl(2,2,2-trifluoroethyl)phosphoric acid as an electrolyte, of the present example was prepared.

Comparative Example 2

In the same manner as in Example 18, except that triethylmethylammonium ethyl(2,2,2-trifluoroethyl)phosphoric acid of Example 18 was not added and the addition was performed such that the concentration of tetraethylammonium tetrafluoroborate became 1.0 mol/liter in the present comparative example, a non-aqueous electrolytic solution for electric double layer capacitors was prepared.

(Evaluation of Electrochemical Characteristics of Electric Double Layer Capacitor)

Electrochemical characteristics of electric double layer capacitors using each of non-aqueous electrolytic solutions of Example 18 and Comparative Example 2 were evaluated. In the evaluation, a coin-shaped cell illustrated in FIG. 1 was used.

<Assembling of Electric Double Layer Capacitor>

As the positive electrode 1 and the negative electrode 2 in the coin-shaped cell, electrodes produced in the following manner were used. That is, an electrode, which is obtained by making active carbon having a specific surface area of 2,000 m$^2$/g obtained by an activation treatment through an activation method using water vapor, together with an auxiliary conductive agent and a binder into a paste form, applying the paste onto a current collector made of an aluminum foil, drying the paste, making the dried paste into a sheet form, and then cutting out the sheet into a 1-cm square piece, was used as a positive electrode 1 and a negative electrode 2.

As illustrated in FIG. 1, assembling of the coin-shaped cell was performed so that, in an internal space formed by a positive electrode can 4 and a negative electrode can 5, a stacked body is held in the stacked body in which a positive electrode 1, a separator 3, a negative electrode 2, and a spacer 7 are stacked in this order from the positive electrode can 4-side of the body. The positive electrode 1, the negative electrode 2, and the separator 3 are impregnated with the non-aqueous electrolytic solution.

As an electrochemical measuring instrument, PGSTAT302N manufactured by Metrohm Autolab was used to carry out cyclic voltammetry measurements and AC impedance measurements. All operations from assembling of the coin-shaped cell to the measurements were made in the argon glove box, which had a dew point of −70° C. or lower.

<Evaluation of Positive Electrode Internal Resistance of Electric Double Layer Capacitor>

After the temperature of each coin-shaped cell was kept at 25° C., the cell was charged to 3,400 mV at a charge current of 1.0 mA. Thereafter, the battery was kept at 3,000 mV for 10 minutes. Thereafter, the cell was discharged to 0 mV at a discharge current of 1.0 mV, followed by keeping at 0 mV for 10 minutes. After performing 5 cycles under these charge-discharge conditions, the AC impedance was measured, followed by comparison and evaluation about the internal resistance of the capacitor. The resistance when using the non-aqueous electrolytic solution of Comparative Example 2 was regarded as 100, and the ratio of the internal resistance of the positive electrode 1 in the non-aqueous electrolytic solution of Example 18 is shown in Table 3 below.

TABLE 3

| | Non-aqueous electrolytic solution | | Internal resistance ratio after 5 cycles |
|---|---|---|---|
| | Electrolyte | Additive | |
| Example 18 | Triethylmethylammonium ethyl(2,2,2-trifluoroethyl)phosphoric acid | — | 90 |

TABLE 3-continued

| | Non-aqueous electrolytic solution | | Internal resistance ratio after 5 cycles |
|---|---|---|---|
| | Electrolyte | Additive | |
| Comparative Example 2 | Triethylmethylammonium tetrafluoroborate | — | 100 |

DESCRIPTION OF REFERENCE SIGNS

1 Positive electrode
2 Negative electrode
3 Separator
4 Positive electrode can
5 Negative electrode can
6 Gasket
7 Spacer
8 Spring
10 Aluminum block
11 Stainless steel supporting rod
12 Stainless steel supporting rod
13 Stainless steel supporting rod
14 Teflon lid
15 Glass container
16 Non-aqueous electrolytic solution
17 Working electrode
18 Reference electrode
19 Counter electrode

What is claimed is:

1. A power storage element comprising a non-aqueous electrolytic solution, which comprises, as an electrolyte, a phosphoric acid diester salt represented by the following chemical formula (1):

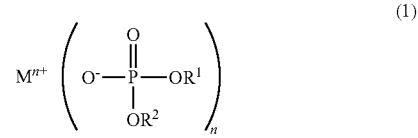

wherein $M^{n+}$ represents a hydrogen ion, an alkali metal ion, an alkali earth metal ion, an aluminum ion, a transition metal ion, or an onium ion; $R^1$ and $R^2$ are different from each other and represent a hydrocarbon group having 1 to 10 carbon atoms, or a hydrocarbon group having 1 to 10 carbon atoms and having at least one of a halogen atom, a heteroatom, and an unsaturated bond; and n represents a valence.

2. The power storage element according to claim 1, wherein either one of $R^1$ and $R^2$ is an alkyl group having 1 to 10 carbon atoms and having a halogen atom, and other one is an alkyl group having 1 to 10 carbon atoms and having no halogen atom.

3. The power storage element according to claim 1, wherein either one of $R^1$ and $R^2$ is a 2,2,2-trifluoroethyl group, and the other one is an ethyl group.

4. The power storage element according to claim 1, wherein M is at least one selected from the group consisting of lithium, sodium, magnesium, and calcium.

5. The power storage element according to claim 1, wherein M is triethylmethylammonium, tetraethylammonium, 1-ethyl-3-methylimidazolium, or 1-ethyl-2methylpyrrolidinium.

* * * * *